United States Patent
Chun et al.

(10) Patent No.: US 9,840,739 B2
(45) Date of Patent: Dec. 12, 2017

(54) METHOD FOR DETERMINING SNP GENOTYPE

(71) Applicant: SEEGENE, INC., Seoul (KR)

(72) Inventors: Jong Yoon Chun, Seoul (KR); Young Jo Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 0 days.

(21) Appl. No.: 14/908,329

(22) PCT Filed: Jul. 30, 2014

(86) PCT No.: PCT/KR2014/007004
§ 371 (c)(1),
(2) Date: Jan. 28, 2016

(87) PCT Pub. No.: WO2015/016612
PCT Pub. Date: Feb. 5, 2015

(65) Prior Publication Data
US 2016/0273041 A1    Sep. 22, 2016

Related U.S. Application Data

(60) Provisional application No. 61/860,294, filed on Jul. 31, 2013.

(51) Int. Cl.
*C12Q 1/68* (2006.01)

(52) U.S. Cl.
CPC ......... *C12Q 1/6883* (2013.01); *C12Q 1/6827* (2013.01); *C12Q 1/6858* (2013.01); *C12Q 2600/156* (2013.01)

(58) Field of Classification Search
None
See application file for complete search history.

(56) References Cited

U.S. PATENT DOCUMENTS

| 5,691,142 A | 11/1997 | Dahlberg et al. |
| 6,893,819 B1 | 5/2005 | Sorge |
| 2013/0109588 A1 | 5/2013 | Chun et al. |

FOREIGN PATENT DOCUMENTS

| WO | 2002079518 A1 | 10/2002 |
| WO | 2012150749 A1 | 11/2012 |

OTHER PUBLICATIONS

French, D.J., et al., HyBeacon™ probes: a new tool for DNA sequence detection and allele discrimination, Molecular and Cellular Probes, Academic Press, London, GB, vol. 15, No. 6, Dec. 1, 2001, pp. 363-374.

*Primary Examiner* — James Martinell
(74) *Attorney, Agent, or Firm* — Gianna Julian-Arnold; Saul Ewing LLP

(57) ABSTRACT

The present invention is generally drawn to a novel method for determining a SNP (single nucleotide polymorphism) genotype using a PTO-SNV (Probing and Tagging Oligonucleotide for Single Nucleotide Variation). The present invention provides novel protocols for SNP genotyping in which only one allele-specific oligonucleotide permits in a SNP genotyping reaction to determine whether a target nucleic acid sequence to be analyzed is homozygous or heterozygous for the SNP allele of interest or has no SNP allele of interest.

20 Claims, 4 Drawing Sheets

Fig. 1
A. Probing and Tagging Oligonucleotide for Single Nucleotide Variation (PTO-SNV)
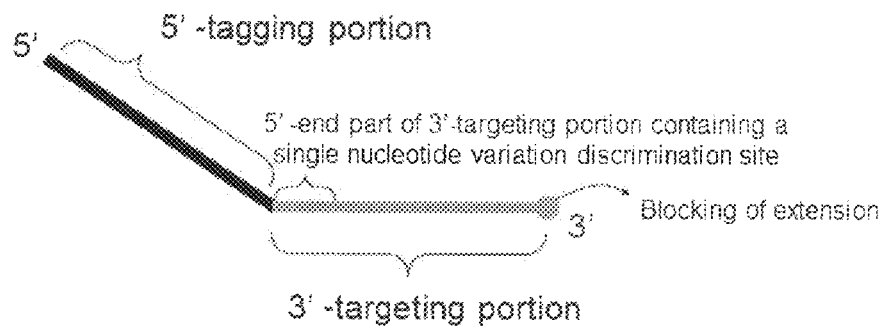
B. Capturing and Templating Oligonucleotide (CTO)
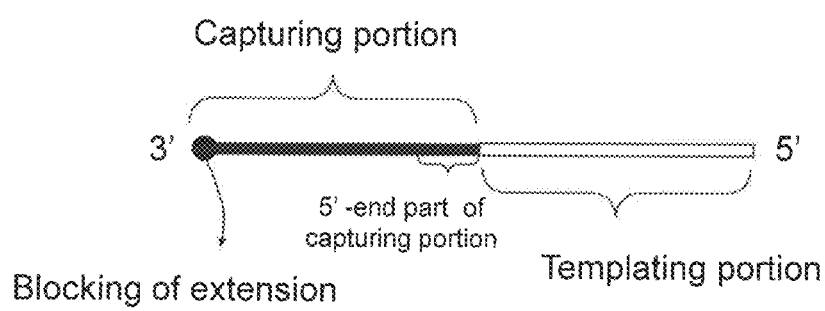

Fig. 2

PTO-SNV for detecting mutant allele

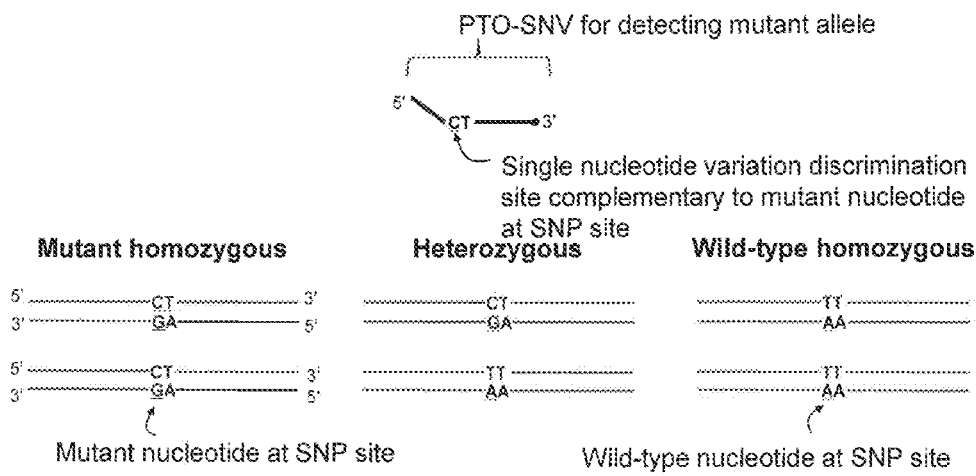

Single nucleotide variation discrimination site complementary to mutant nucleotide at SNP site Mutant homozygous | Heterozygous | Wild-type homozygous Mutant nucleotide at SNP site | Wild-type nucleotide at SNP site

PTO-SNV Hybridization

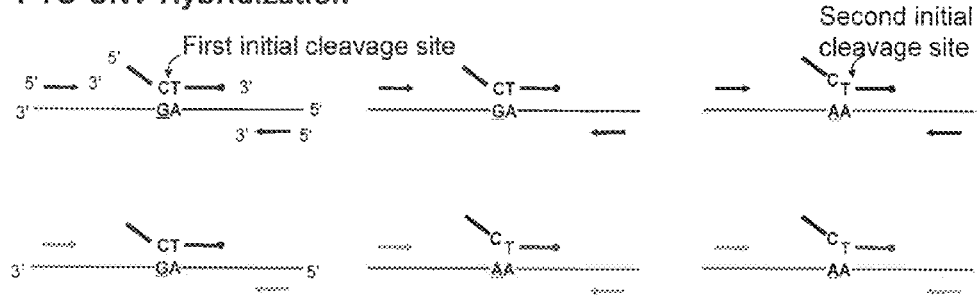

First initial cleavage site | Second initial cleavage site

Primer extension & Cleavage of PTO-SNV

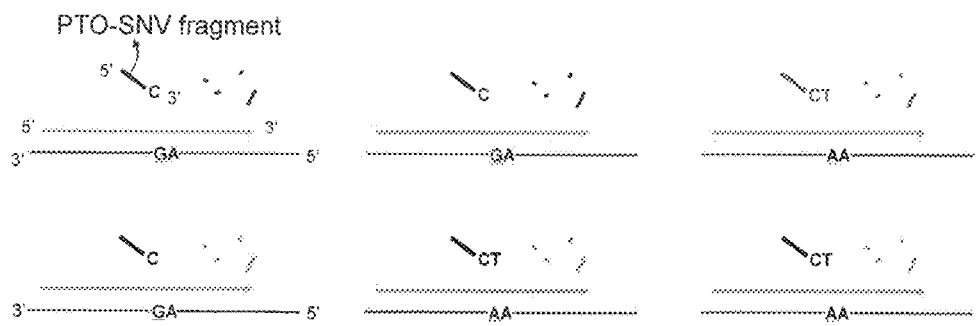

PTO-SNV fragment

Hybridization of PTO-SNV fragment to CTO & Extension

Detection of extended strand and determination of SNP genotyping

METHOD FOR DETERMINING SNP GENOTYPE

CROSS REFERENCE TO RELATED APPLICATIONS

This application claims the priority of PCT/KR2014/007004, filed on Jul. 30, 2014, which claims priority to U.S. Patent Application No. 61/860,294, filed Jul. 31, 2013, the entire contents of each of which are hereby incorporated in total by reference.

SEQUENCE LISTING

This application incorporates by reference the Sequence Listing contained in an ASCII text file named "361406_00029_SeqList.txt" submitted via EFS-Web. The text file was created on Jan. 27, 2016, and is 2 kb in size.

BACKGROUND OF THE INVENTION

Field of the Invention

The present invention relates to methods for determining a SNP (single nucleotide polymorphism) genotype.

Description of the Related Art

DNA hybridization is a fundamental process in molecular biology and is affected by ionic strength, base composition, length of fragment to which the nucleic acid has been reduced, the degree of mismatching, and the presence of denaturing agents. DNA hybridization-based technologies would be a very useful tool in specific nucleic acid sequence determination and clearly be valuable in clinical diagnosis, genetic research, and forensic laboratory analysis.

However, the conventional methods and processes depending mostly on hybridization are very likely to produce false positive results due to non-specific hybridization between probes and non-target sequences. Therefore, there remain problems to be solved for improving their reliability.

Besides probe hybridization processes, several approaches using additional enzymatic reactions, for example, TaqMan™ probe method, have been suggested.

In TaqMan™ probe method, the labeled probe hybridized with a target nucleic acid sequence is cleaved by a 5' nuclease activity of an upstream primer-dependent DNA polymerase, generating a signal indicating the presence of a target sequence (U.S. Pat. Nos. 5,210,015, 5,538,848 and 6,326,145). The TaqMan™ probe method suggests two approaches for signal generation: polymerization-dependent cleavage and polymerization-independent cleavage. In polymerization-dependent cleavage, extension of the upstream primer must occur before a nucleic acid polymerase encounters the 5'-end of the labeled probe. As the extension reaction continues, the polymerase progressively cleaves the 5'-end of the labeled probe. In polymerization-independent cleavage, the upstream primer and the labeled probe are hybridized with a target nucleic acid sequence in close proximity such that binding of the nucleic acid polymerase to the 3'-end of the upstream primer puts it in contact with the 5'-end of the labeled probe to release the label. In addition, the TaqMan™ probe method discloses that the labeled probe at its 5'-end having a 5'-tail region not-hybridizable with a target sequence is also cleaved to form a fragment comprising the 5'-tail region.

There have been reported some methods in which a probe having a 5'-tail region non-complementary to a target sequence is cleaved by 5' nuclease to release a fragment comprising the 5'-tail region.

For instance, U.S. Pat. No. 5,691,142 discloses a cleavage structure to be digested by 5' nuclease activity of DNA polymerase. The cleavage structure is exemplified in which an oligonucleotide comprising a 5' portion non-complementary to and a 3' portion complementary to a template is hybridized with the template and an upstream oligonucleotide is hybridized with the template in close proximity. The cleavage structure is cleaved by DNA polymerase having 5' nuclease activity or modified DNA polymerase with reduced synthetic activity to release the 5' portion non-complementary to the template. The released 5' portion is then hybridized with an oligonucleotide having a hairpin structure to form a cleavage structure, thereby inducing progressive cleavage reactions to detect a target sequence.

U.S. Pat. No. 7,381,532 discloses a process in which the cleavage structure having the upstream oligonucleotide with blocked 3'-end is cleaved by DNA polymerase having 5' nuclease activity or FEN nuclease to release non-complementary 5' flap region and the released 5' flap region is detected by size analysis or interactive dual label. U.S. Pat. No. 6,893,819 discloses that detectable released flaps are produced by a nucleic acid synthesis dependent, flap-mediated sequential amplification method. In this method, a released flap from a first cleavage structure cleaves, in a nucleic acid synthesis dependent manner, a second cleavage structure to release a flap from the second cleavage structure and the release flaps are detected. U.S. Pat. No. 7,309,573 disclose a method including formation of a released flap produced by a nucleic acid synthesis; extension of the released flap; cleavage of an oligonucleotide during extension of the flap and detection of a signal generated by the cleavage of the oligonucleotide.

By hybridization of fluorescence-labeled probes in a liquid phase, a plurality of target nucleic acid sequences may be simultaneously detected using even a single type of a fluorescent label by melting curve analysis. However, the conventional technologies for detection of target sequences by 5' nuclease-mediated cleavage of interactive-dual labeled probes require different types of fluorescent labels for different target sequences in multiplex target detection, which limits the number of target sequences to be detected due to limitation of the number of types of fluorescent labels.

U.S. Pat. Appln. Pub. 2008-0241838 discloses a target detection method using cleavage of a probe having a 5' portion non-complementary to a target nucleic acid sequence and hybridization of a capture probe. A label is positioned on the non-complementary 5' portion. The labeled probe hybridized with the target sequence is cleaved to release a fragment, after which the fragment is then hybridized with the capture probe to detect the presence of the target sequence. In this method, it is necessary that an uncleaved/intact probe is not hybridized with the capture probe. For that, the capture probe having a shorter length has to be immobilized onto a solid substrate. However, such a limitation results in lower efficiency of hybridization on a solid substrate and also in difficulties in optimization of reaction conditions.

Therefore, there remain long-felt needs in the art to develop novel approaches for detection of a target sequence, preferably multiple target sequences, in a liquid phase and on a solid phase by not only hybridization but also enzymatic reactions such as 5' nucleolytic reaction in a more convenient, reliable and reproducible manner. Furthermore, a novel target detection method not limited by the number of types of labels (particularly, fluorescent labels) is also needed in the art.

In the meantime, nucleotide variations are important in the research and clinical fields. Of them, single nucleotide polymorphisms (SNPs) are most commonly found in a human genome and serve as markers for disease-related loci and pharmacogenetics (Landegren et al., 1998; Roses, 2000). SNPs are found at the rate of approximately 1 per 1000 bp in a human genome and their total number is estimated about three millions. For the detection of nucleotide variations such as SNP, deletion, insertion and translocation, various allelic discrimination technologies have been reported.

The allele-specific TaqMan probe is designed such that it is hybridized only with perfectly matched target sequences in extension step of PCR. The TaqMan probe has a reporter molecule and a quencher molecule capable of quenching the fluorescent signal from the reporter molecule. The TaqMan probe hybridized with target sequences is digested by 5' nuclease activity of Taq DNA polymerase and the reporter molecule and the quencher molecule are separated to generate a target signal. For allelic discrimination, 13-20 mer probes conjugated with minor groove binder (MGB) are used (Livak, et al., Genet. Anal. 14:143-149(1999)). Since the allelic discrimination method using the TaqMan probe employs not only hybridization reaction but also enzymatic reactions of 5' nuclease activity, its specificity is enhanced. However, the method has serious troublesome such as difficulties in allelic-specific probe design and optimized reaction conditions which have to discriminate difference by one mismatch. In addition, the conjugate with MGB is one of troubleshootings in the allele-specific TaqMan probe.

In SNP genotyping for clinical samples containing nucleic acid molecules carrying SNP, it is conventional to perform genotyping in individually two detection reactions using two probes each specific to an allele (Kostrikis et al., Science (1998) 279: 1228-1229). Therefore, there are limitations by demand of two types of probes for individual detection of each allele. As another approach, a melting peak analysis was employed using a single type of a probe to be hybridized with alleles with different $T_m$ values, which shows different melting peak patterns for genotyping (French et. al., Molecular and Cellular Probes (2001) 15: 363-374). Although the melting peak analysis is advantageous in view of use of a single type of probe, it has poor applicability to multiplex detection of a plurality of SNPs because melting peaks with different $T_m$ values corresponding to a plurality of SNPs are generated.

Therefore, there remain long-felt needs in the art to develop novel approaches for determining a SNP genotyping in a more convenient, reliable and reproducible manner, which is capable of being free from shortcomings of the conventional technologies.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel methods for SNP genotyping by using only one allele-specific oligonucleotide, e.g. an allele-specific probe for detecting only a single type of SNP nucleotides found in a SNP site. As a result, the present inventors have established novel protocols for SNP genotyping in which only one allele-specific oligonucleotide permits in a SNP genotyping reaction to determine whether a target nucleic acid sequence to be analyzed is homozygous or heterozygous for the SNP allele of interest or has no SNP allele of interest.

Therefore, it is an object of this invention to provide a method for determining a SNP (single nucleotide polymorphism) genotype.

It is another object of this invention to provide a kit for determining a SNP (single nucleotide polymorphism) genotype.

Other objects and advantages of the present invention will become apparent from the detailed description to follow taken in conjugation with the appended claims and drawings.

BRIEF DESCRIPTION OF THE DRAWINGS

FIG. 1A and FIG. 1B show the schematic structures of PTO-SNV used in the present invention. Preferably, the 3'-ends of the PTO-SNV and CTO are blocked to prohibit their extension. FIG. 1A shows Probing and Tagging Oligonucleotide for Single Nucleotide Variation. FIG. 1B shows CTO (Capturing and Templating Oligonucleotide).

FIGS. 2 and 3 schematically represent the present method for determining a SNP (single nucleotide polymorphism) genotype.

DETAILED DESCRIPTION OF THIS INVENTION

Figure 3:
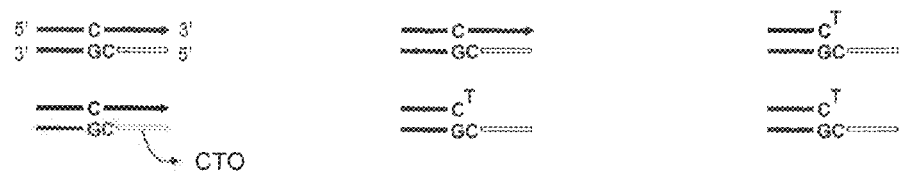

In an aspect of the present invention, there is provided a method for determining a SNP (single nucleotide polymorphism) genotype, comprising:

(a) hybridizing a target nucleic acid sequence containing a SNP with an upstream oligonucleotide and a PTO-SNV (Probing and Tagging Oligonucleotide for Single Nucleotide Variation); wherein the upstream oligonucleotide comprises a hybridizing nucleotide sequence complementary to the target nucleic acid sequence; the PTO-SNV comprises (i) a 3'-targeting portion comprising a hybridizing nucleotide sequence complementary to the target nucleic acid sequence, (ii) a 5'-tagging portion comprising a nucleotide sequence non-complementary to the target nucleic acid sequence, and (iii) a single nucleotide variation discrimination site comprising a nucleotide complementary to a SNP nucleotide at a SNP site of the SNP allele of interest on the target nucleic acid sequence, positioned on a 5'-end part of the 3'-targeting portion; wherein the 3'-targeting portion is hybridized with the target nucleic acid sequence and the 5'-tagging portion is not hybridized with the target nucleic acid sequence; the upstream oligonucleotide is located upstream of the PTO-SNV; the upstream oligonucleotide or its extended strand induces cleavage of the PTO-SNV by an enzyme having a 5' nuclease activity;

(b) contacting the resultant of the step (a) to an enzyme having a 5' nuclease activity under conditions for cleavage of the PTO-SNV; wherein when the PTO-SNV is hybridized with the SNP allele of interest having the SNP nucleotide complementary to the single nucleotide variation discrimination site, the 5'-end part of the 3'-targeting portion forms a double strand with the target nucleic acid sequence to induce cleavage from a first initial cleavage site, and a first fragment is released; wherein when the PTO-SNV is hybridized with a different SNP allele from the SNP allele of interest having a SNP nucleotide non-complementary to the single nucleotide variation discrimination site, the 5'-end part of the 3'-targeting portion does not form a double strand with the target nucleic acid sequence to induce cleavage from a second initial cleavage site located downstream of the first initial cleavage site, and a second fragment is released; wherein the second fragment comprises an additional 3'-end portion allowing the second fragment different from the first fragment;

(c) hybridizing the fragment released from the PTO-SNV with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO-SNV and (ii) a templating portion comprising a nucleotide sequence non-complementary to the 5'-tagging portion and the 3'-targeting portion of the PTO-SNV; wherein the first fragment or the second fragment released from the PTO-SNV is hybridized with the capturing portion of the CTO;

(d) performing an extension reaction using the resultant of the step (c) and a template-dependent nucleic acid polymerase; wherein when the first fragment is hybridized with the capturing portion of the CTO, it is extended to form an extended strand comprising an extended sequence complementary to the templating portion of the CTO; wherein when the second fragment is hybridized with the capturing portion of the CTO, it is not extended;

(e) detecting a signal indicating the presence of the extended strand; wherein the signal shows higher intensity for the target nucleic acid sequence homozygous for the SNP allele of interest than that of the target nucleic acid sequence heterozygous for the SNP allele of interest, and the signal is not provided from the target nucleic acid sequence having no SNP allele of interest; and (f) determining a SNP genotype in the target nucleic acid sequence by the intensity of the signal detected in the step (e).

The present inventors have made intensive researches to develop novel methods for SNP genotyping by using only one allele-specific oligonucleotide, e.g. an allele-specific probe for detecting only a single type of SNP nucleotides found in a SNP site. As a result, the present inventors have established novel protocols for SNP genotyping in which only one allele-specific oligonucleotide permits in a SNP genotyping reaction to determine whether a target nucleic acid sequence to be analyzed is homozygous or heterozygous for the SNP allele of interest or has no SNP allele of interest. Where there is found two SNP nucleotides at a SNP site, the present method allows determining all of three SNP genotypes by use of only one allele-specific oligonucleotide, i.e. only one allele-specific PTO-SNV in a SNP genotyping reaction, which has not been accomplished yet before the present invention. Such technical feature makes SNP genotyping more convenient, inter alia, in a multiplex SNP genotyping.

According to conventional technologies thus far reported, it is common sense that different SNP alleles are detected using different allele-specific oligonucleotides. Given that different SNP alleles can be detected using only single allele-specific oligonucleotide, a SNP genotyping takes a giant step in terms of convenience and multiplexing detection. The present invention breaks through the common sense to propose novel SNP genotyping method in much more convenient and high-throughput manner.

Furthermore, it has been known to one of skill in the art that a probe sequence adjacent to a sequence opposed to a SNP extremely affects probe hybridization. The conventional probes have a sequence opposed to a SNP generally in their middle portion. In this regard, the conventional probes may not select a surrounding sequence around a SNP involved in hybridization. The conventional technologies have serious limitations due to surrounding sequences to SNPs.

Unlikely, in the present invention, the nucleotide variation discrimination site opposed to a SNP is positioned on a 5'-end part of a hybridization-involving portion of probes, such that a sequence of probes to a SNP 5'-adjacent sequence becomes adjustable. Because the influences of a surrounding sequence around a SNP on hybridization are accurately controlled in the present invention, it becomes true to analyze SNPs not or little detectable by conventional technologies due to the influences of a surrounding sequence around a SNP.

The present invention employs successive events followed by PTO-SNV hybridization; cleavage of PTO-SNV (Probing and Tagging Oligonucleotide for Single Nucleotide Variation) and extension; formation of a nucleotide variation-dependent extended strand; detection of the extended strand; and determining a SNP genotype.

Step (a): Hybridization of an Upstream Oligonucleotide and a PTO-SNV with a Target Nucleic Acid Sequence According to the present invention, a target nucleic acid sequence containing a SNP is hybridized with an upstream oligonucleotide and a PTO-SNV (Probing and Tagging Oligonucleotide for Single Nucleotide Variation).

The term used herein "target nucleic acid", "target nucleic acid sequence" or "target sequence" refers to a nucleic acid sequence of interest for detection, which is annealed to or hybridized with a probe or primer under hybridization, annealing or amplifying conditions.

In the present method for SNP genotyping, the target nucleic acid sequence contains at least one SNP site. The target nucleic acid sequence is determined as the wild type allele or mutant allele depending on the type of a nucleotide at the SNP site. In samples of diploid organisms to be analyzed, the combination of the target nucleic acid sequences containing a SNP in the sample may be any one of genotypes; wild type homozygote, heterozygote and mutant homozygote.

The term used herein "probe" refers to a single-stranded nucleic acid molecule comprising a portion or portions that are substantially complementary to a target nucleic acid sequence.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

Preferably, the probe and primer are single-stranded deoxyribonucleotide molecules. The probes or primers used in this invention may be comprised of naturally occurring dNMP (i.e., dAMP, dGM, dCMP and dTMP), modified nucleotide, or non-natural nucleotide. The probes or primers may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term used "hybridizing" used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

The hybridization of a target nucleic acid sequence with the upstream oligonucleotide and the PTO-SNV may be carried out under suitable hybridization conditions routinely determined by optimization procedures. Conditions such as temperature, concentration of components, hybridization and washing times, buffer components, and their pH and ionic strength may be varied depending on various factors, including the length and GC content of oligonucleotide (upstream oligonucleotide and PTO-SNV) and the target nucleotide sequence. For instance, when a relatively short oligonucleotide is used, it is preferable that low stringent conditions are adopted. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999).

There is no intended distinction between the terms "annealing" and "hybridizing", and these terms will be used interchangeably.

The upstream oligonucleotide and PTO-SNV have hybridizing nucleotide sequences complementary to the target nucleic acid sequence. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", preferably perfectly complementary.

The 5'-tagging portion of the PTO-SNV has a nucleotide sequence non-complementary to the target nucleic acid sequence. The templating portion of the CTO (Capturing and Templating Oligonucleotide) has a nucleotide sequence non-complementary to the 5'-tagging portion and the 3'-targeting portion of the PTO. The term "non-complementary" is used herein to mean that primers or probes are sufficiently non-complementary not to hybridize selectively to a target nucleic acid sequence under the designated annealing conditions or stringent conditions, encompassing the terms "substantially non-complementary" and "perfectly non-complementary", preferably perfectly non-complementary.

For example, the term "non-complementary" in conjunction with the 5'-tagging portion of the PTO-SNV means that the 5'-tagging portion is sufficiently non-complementary not to hybridize selectively to a target nucleic acid sequence under the designated annealing conditions or stringent conditions, encompassing the terms "substantially non-complementary" and "perfectly non-complementary", preferably perfectly non-complementary.

The term used herein "PTO-SNV (Probing and Tagging Oligonucleotide for Single Nucleotide Variation)" means an oligonucleotide comprising (i) a 3'-targeting portion comprising a hybridizing nucleotide sequence complementary to the target nucleic acid sequence, (ii) a 5'-tagging portion comprising a nucleotide sequence non-complementary to the target nucleic acid sequence, and (iii) a single nucleotide variation discrimination site comprising a nucleotide complementary to a SNP nucleotide at a SNP site of the SNP allele of interest on the target nucleic acid sequence, positioned on a 5'-end part of the 3'-targeting portion. The PTO-SNV is schematically illustrated in FIG. 1.

The 5'-tagging portion is nucleolytically released from the PTO-SNV after hybridization with the target nucleic acid sequence. The 5'-tagging portion and the 3'-targeting portion in the PTO-SNV have to be positioned in a 5' to 3' order.

The PTO-SNV may be appreciated as one application form of the PTO for detection of single nucleotide variations, which is constructed by introduction of the single nucleotide variation discrimination site into the 5'-end part of the 3'-targeting portion.

The PTO-SNV comprises the single nucleotide variation discrimination site comprising a nucleotide complementary to a SNP nucleotide at a SNP site of the SNP allele of interest on the target nucleic acid sequence, positioned on a 5'-end part of the 3'-targeting portion.

Where the PTO-SNV is hybridized with the SNP allele of interest having the SNP nucleotide complementary to the single nucleotide variation discrimination site, the 5'-end part of the 3'-targeting portion forms a double strand with the target nucleic acid sequence. Where the PTO-SNV is hybridized with a different SNP allele from the SNP allele of interest having a SNP nucleotide non-complementary to the single nucleotide variation discrimination site, the 5'-end part of the 3'-targeting portion does not form a double strand with the target nucleic acid sequence. Such distinct hybridization patterns on the nucleotide variation of interest are responsible for differences in cleavage sites of the PTO-SNV, thereby producing two types of PTO-SNV fragments to give signal differentiation depending on the presence of the SNP allele of interest. The 5'-end part of the 3'-targeting portion of the PTO-SNV may be also described as a single strand-forming 5'-end portion of the 3'-targeting portion of the PTO-SNV when hybridized with a different SNP allele from the SNP allele of interest having a SNP nucleotide non-complementary to the single nucleotide variation discrimination site.

The single nucleotide variation discrimination site positioned on a 5'-end part of the 3'-targeting portion of the PTO-SNV comprises a nucleotide complementary to a SNP nucleotide in a SNP site of the SNP allele of interest on the target nucleic acid sequence.

According to an embodiment, the single nucleotide variation discrimination site is located within 10 nucleotides, particularly 8 nucleotides, more particularly 6 nucleotides, still more particularly 4 nucleotides, 3 nucleotides, 2 nucleotides or 1 nucleotide apart from the 5'-end of the 3'-targeting portion of the PTO-SNV. Particularly, the single nucleotide variation discrimination site is located at the 5'-end of the 3'-targeting portion of the PTO-SNV.

The location of the single nucleotide variation discrimination site may be determined in consideration of sequences to be detected, type of nucleases and reaction conditions.

In the illustrative FIG. 2, the target nucleic acid sequence may be either the mutant allele having a "G" nucleotide or the wild-type allele having an "A" nucleotide at the SNP site. The PTO-SNV has in its single nucleotide variation discrimination site a "C" nucleotide complementary to the SNP nucleotide, "G" nucleotide at the SNP site of the mutant allele. In this case, the "SNP allele of interest" to be detected refers to the mutant allele, and the "different SNP allele from the SNP allele of interest" refers to the wild-type allele.

The term used herein "SNP allele of interest" refers to an allele to be detected by the PTO-SNV. The "different SNP allele from the SNP allele of interest" refers to allele(s) other than an allele to be detected by the PTO-SNV. Unless otherwise indicated, the terms "different SNP allele" and "different SNP allele from the SNP allele of interest" are used interchangeably.

In the present method, the term "SNP allele" may be used to refers to the identity of the nucleotide at a SNP site (e.g., whether the SNP site has a G, A, T or C) on the target nucleic acid sequence.

Particularly, the hybridization in step (a) is preformed under stringent conditions that the 3'-targeting portion is hybridized with the target nucleic acid sequence and the 5'-tagging portion is not hybridized with the target nucleic acid sequence.

The PTO-SNV does not require any specific lengths. For example, the length of the PTO-SNV may be 15-150 nucleotides, 15-100 nucleotides, 15-80 nucleotides, 15-60 nucleotides, 15-40 nucleotides, 20-150 nucleotides, 20-100 nucleotides, 20-80 nucleotides, 20-60 nucleotides, 20-50 nucleotides, 30-150 nucleotides, 30-100 nucleotides, 30-80 nucleotides, 30-60 nucleotides, 30-50 nucleotides, 35-100 nucleotides, 35-80 nucleotides, 35-60 nucleotides, or 35-50 nucleotides. The 3'-targeting portion of the PTO-SNV may be in any lengths so long as it is specifically hybridized with target nucleic acid sequences. For example, the 3'-targeting portion of the PTO-SNV may be 10-100 nucleotides, 10-80 nucleotides, 10-50 nucleotides, 10-40 nucleotides, 10-30 nucleotides, 15-100 nucleotides, 15-80 nucleotides, 15-50 nucleotides, 15-40 nucleotides, 15-30 nucleotides, 20-100 nucleotides, 20-80 nucleotides, 20-50 nucleotides, 20-40 nucleotides or 20-30 nucleotides in length. The 5'-tagging portion may be in any lengths so long as it is specifically hybridized with the capturing portion of the CTO and then extended. For instance, the 5'-tagging portion of the PTO-SNV may be 5-50 nucleotides, 5-40 nucleotides, 5-30 nucleotides, 5-20 nucleotides, 10-50 nucleotides, 10-40 nucleotides, 10-30 nucleotides, 10-20 nucleotides, 15-50 nucleotides, 15-40 nucleotides, 15-30 nucleotides or 15-20 nucleotides in length.

The 3'-end of the PTO-SNV may have a 3'-OH terminal. Preferably, the 3'-end of the PTO-SNV is "blocked" to prohibit its extension.

The blocking may be achieved in accordance with conventional methods. For instance, the blocking may be performed by adding to the 3'-hydroxyl group of the last nucleotide a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

Alternatively, the PTO-SNV may be designed to have a hairpin structure.

The non-hybridization between the 5'-tagging portion of the PTO-SNV and the target nucleic acid sequence refers to non-formation of a stable double-strand between them under certain hybridization conditions. According to an embodiment, the 5'-tagging portion of the PTO-SNV not involved in the hybridization with the target nucleic acid sequence forms a single-strand.

The upstream oligonucleotide is located upstream of the PTO-SNV.

In addition, the upstream oligonucleotide or its extended strand hybridized with the target nucleic acid sequence induces cleavage of the PTO-SNV by an enzyme having a 5' nuclease activity.

The induction of the PTO-SNV cleavage by the upstream oligonucleotide may be accomplished by two fashions: (i) upstream oligonucleotide extension-independent cleavage induction; and (ii) upstream oligonucleotide extension-dependent cleavage induction.

Where the upstream oligonucleotide is positioned adjacently to the PTO-SNV sufficient to induce the PTO-SNV cleavage by an enzyme having a 5' nuclease activity, the enzyme bound to the upstream oligonucleotide digests the PTO-SNV with no extension reaction. In contrast, where the upstream oligonucleotide is positioned distantly to the PTO-SNV, an enzyme having a polymerase activity (e.g., template-dependent polymerase) catalyzes extension of the upstream oligonucleotide (e.g., upstream primer) and an enzyme having a 5' nuclease activity bound to the extended product digests the PTO-SNV.

Therefore, the upstream oligonucleotide may be located relatively to the PTO-SNV in two fashions. The upstream oligonucleotide may be located adjacently to the PTO-SNV sufficient to induce the PTO-SNV cleavage in an extension-independent manner. Alternatively, the upstream oligonucleotide may be located distantly to the PTO-SNV sufficient to induce the PTO-SNV cleavage in an extension-dependent manner.

The term used herein "adjacent" with referring to positions or locations means that the upstream oligonucleotide is located adjacently to the 3'-targeting portion of the PTO-SNV to form a nick. Also, the term means that the upstream oligonucleotide is located 1-30 nucleotides, 1-20 nucleotides or 1-15 nucleotides apart from the 3'-targeting portion of the PTO.

The term used herein "distant" with referring to positions or locations includes any positions or locations sufficient to ensure extension reactions.

According to an embodiment, the upstream oligonucleotide is located distantly to the PTO-SNV sufficient to induce the PTO-SNV cleavage in an extension-dependent manner.

According to an embodiment, the upstream oligonucleotide is an upstream primer or an upstream probe. The upstream primer is suitable in an extension-independent cleavage induction or an extension-dependent cleavage, and the upstream probe is suitable in an extension-independent cleavage induction.

Alternatively, the upstream oligonucleotide may have a partial-overlapped sequence with the 5'-part of the 3'-targeting portion of the PTO-SNV. Preferably, the overlapped sequence is 1-10 nucleotides, more preferably 1-5 nucleotides, still more preferably 1-3 nucleotides in length. Where the upstream oligonucleotide has a partial-overlapped sequence with the 5'-part of the 3'-targeting portion of the PTO-SNV, the 3'-targeting portion is partially digested along with the 5'-tagging portion in the cleavage reaction of the step (b). In addition, the overlapped sequence permits to cleave a desired site of the 3'-targeting portion.

According to an embodiment, the upstream primer induces through its extended strand the cleavage of the PTO-SNV by the enzyme having the 5' nuclease activity.

The conventional technologies for cleavage reactions by upstream oligonucleotides may be applied to the present invention, so long as the upstream oligonucleotide induces cleavage of the PTO-SNV hybridized with the target nucleic acid sequence to release a fragment comprising the 5'-tagging portion or a part of the 5'-tagging portion of the PTO-SNV. For example, U.S. Pat. Nos. 5,210,015, 5,487,972, 5,691,142, 5,994,069 and 7,381,532 and U.S. Appln. Pub. No. 2008-0241838 may be applied to the present invention.

According to an embodiment, the method is performed in the presence of a downstream primer. The downstream primer generates additionally a target nucleic acid sequence to be hybridized with the PTO-SNV, enhancing sensitivity in a target detection.

According to an embodiment, when the upstream primer and the downstream primer are used, a template-dependent nucleic acid polymerase is additionally employed for extension of the primers.

According to an embodiment, the upstream oligonucleotide (upstream primer or upstream probe), the downstream primer and/or 5'-tagging portion of the PTO-SNV have a dual priming oligonucleotide (DPO) structure developed by the present inventor. The oligonucleotides having the DPO structure show significantly improved target specificity compared with conventional primers and probes (see WO 2006/095981; Chun et al., Dual priming oligonucleotide system for the multiplex detection of respiratory viruses and SNP genotyping of CYP2C19 gene, *Nucleic Acid Research*, 35:6e40(2007)).

According to an embodiment, the 3'-targeting portion of the PTO-SNV has a modified dual specificity oligonucleotide (mDSO) structure developed by the present inventor. The modified dual specificity oligonucleotide (mDSO) structure shows significantly improved target specificity compared with conventional probes (see WO 2011/028041)

Step (b): Release of a Fragment from the PTO-SNV

Afterwards, the resultant of the step (a) is contacted to an enzyme having a 5' nuclease activity under conditions for cleavage of the PTO-SNV.

The term used herein "conditions for cleavage of the PTO-SNV" means conditions sufficient to digest the PTO-SNV hybridized with the target nucleic acid sequence by the enzyme having the 5' nuclease activity, such as temperature, pH, ionic strength, buffer, length and sequence of oligonucleotides and enzymes. For example, when Taq DNA polymerase is used as the enzyme having the 5' nuclease activity, the conditions for cleavage of the PTO-SNV include Tris-HCl buffer, KCl, $MgCl_2$ and temperature.

Where the PTO-SNV is hybridized with the SNP allele of interest having the SNP nucleotide complementary to the single nucleotide variation discrimination site, the 5'-end part of the 3'-targeting portion forms a double strand with the target nucleic acid sequence to induce cleavage from a first initial cleavage site, and a first fragment is released (see FIG. 2).

Where the PTO-SNV is hybridized with a different SNP allele from the SNP allele of interest having a SNP nucleotide non-complementary to the single nucleotide variation discrimination site, the 5'-end part of the 3'-targeting portion does not form a double strand with the target nucleic acid sequence to induce cleavage from a second initial cleavage site located downstream of the first initial cleavage site, and a second fragment is released; wherein the second fragment comprises an additional 3'-end portion allowing the second fragment different from the first fragment (see FIG. 2).

As such, differences in cleavage sites and types of PTO-SNV fragments generated result in different extension patterns depending on the presence and absence of the single nucleotide variation of interest on the target nucleic acid sequence (i.e., the SNP allele of interest), contributing to differential detection of the single nucleotide variation on the target nucleic acid sequence.

An initial cleavage site of the PTO-SNV is affected by the type of 5' nucleases, the type of upstream oligonucleotides (upstream probe or upstream primer), hybridization sites of upstream oligonucleotides and cleavage conditions.

An initial cleavage site by template dependent polymerase having 5' nuclease activity with extension of upstream primers is generally positioned in a 5' to 3' direction at an initial nucleotide of a double strand (i.e., bifurcation site) in structures including a single strand and a double strand or at 1-2 nucleotides apart from the initial nucleotide. By the cleavage reaction, fragments comprising the 5'-tagging portion and a part of the 3'-targeting portion are produced. Where the present invention is performed by upstream oligonucleotide extension-independent cleavage induction, the cleavage site of the PTO-SNV may be adjusted by location of upstream oligonucleotides (e.g. upstream probe).

The term used herein "a first initial cleavage site" in conjunction with the PTO-SNV means to a cleavage site of the PTO-SNV being firstly cleaved when the PTO-SNV is hybridized with the SNP allele of interest having the SNP nucleotide complementary to the single nucleotide variation discrimination site. The term used herein "a second initial cleavage site" in conjunction with the PTO-SNV means to a cleavage site of the PTO-SNV being firstly cleaved when the PTO-SNV is hybridized with a different SNP allele from the SNP allele of interest having a SNP nucleotide non-complementary to the single nucleotide variation discrimination site.

The term used herein "a first fragment" refers to a fragment produced upon cleavage at the first initial cleavage site. The term is used interchangeably with "a first segment" and "a PTO-SNV first fragment". The term herein "a second fragment" refers to a fragment produced upon cleavage at the second initial cleavage site. The term is used interchangeably with "a second segment" and "a PTO-SNV second fragment".

According to a preferred embodiment, the first fragment and the second fragment each comprises the 5'-tagging portion or a part of the 5'-tagging portion.

The cleavage may successively occur after the cleavage of the first initial cleavage site (or the second initial cleavage site) depending on cleavage methods used. For instance, where 5' nuclease cleavage reaction together with extension of upstream primers is used, the initial cleavage site and its successive sequence are cleaved. Where an upstream probe is used and the cleavage reaction occurs at a site apart from a location site of the probe, the cleavage reaction may occur only at the site and cleavage at successive sites may not occur.

According to an embodiment, an initial cleavage site dependent on extension of upstream primers may be positioned in a 5' to 3' direction at an initial nucleotide of a double strand (i.e., bifurcation site).

As shown in FIG. 2 representing an example of the present invention, the single nucleotide variation discrimination site is positioned at the 5'-end of the 5'-end part of the 3'-targeting portion. In such case, the first initial cleavage site is positioned immediately adjacent, in a 5' to 3' direction, to the 5'-end part of the 3'-targeting portion. In other words, the first initial cleavage site is positioned immediately adjacent, in a 3' direction, to the single nucleotide variation discrimination site. The second initial cleavage site is generally positioned at 1 nucleotide apart, in a 3' direction, from the single nucleotide variation discrimination site.

When the PTO-SNV is hybridized with the target nucleic acid sequence, its 3'-targeting portion is involved in the hybridization and the 5'-tagging portion forms a single-strand with no hybridization with the target nucleic acid sequence. As such, an oligonucleotide comprising both single-stranded and double-stranded structures may be digested using an enzyme having a 5' nuclease activity by a variety of technologies known to one of skill in the art.

The cleavage sites of the PTO-SNV may be varied depending on the type of to upstream oligonucleotides (upstream probe or upstream primer), hybridization sites of upstream oligonucleotides and cleavage conditions (see U.S. Pat. Nos. 5,210,015, 5,487,972, 5,691,142, 5,994,069 and 7,381,532 and U.S. Appln. Pub. No. 2008-0241838).

A multitude of conventional technologies may be employed for the cleavage reaction of the PTO-SNV, releasing a fragment comprising the 5'-tagging portion or a part of the 5'-tagging portion.

Briefly, there may be three sites of cleavage in the step (b). Firstly, the cleavage site is a junction site between a hybridization portion of the PTO-SNV (3'-targeting portion) and a non-hybridization portion (5'-tagging portion). The second cleavage site is a site located several nucleotides in a 3'-direction apart from the 3'-end of the 5'-tagging portion of the PTO-SNV. The second cleavage site is located at the 5'-end part of the 3'-targeting portion of the PTO-SNV. The third cleavage site is a site located several nucleotides in a 5'-direction apart from the 3'-end of the 5'-tagging portion of the PTO-SNV.

By considering cleavage sites dependent on cleavage methods, the single nucleotide variation discrimination site may be suitably located on the PTO-SNV or a sequence of a portion of the CTO to be hybridized with the fragment may be suitably adjusted.

In this regard, the term used herein "a fragment comprising the 5'-tagging portion or a part of the 5'-tagging portion of the PTO-SNV" in conjunction with cleavage of the PTO-SNV by the enzyme having the 5' nuclease activity is used to encompass (i) the 5'-tagging portion, (ii) the 5'-tagging portion and the 5'-end part of the 3'-targeting portion and (iii) a part of the 5'-tagging portion. In this application, the term "a fragment comprising the 5'-tagging portion or a part of the 5'-tagging portion of the PTO-SNV" may be also described as "PTO-SNV fragment".

According to an embodiment, the PTO-SNV has a blocker portion containing as a blocker at least one nucleotide resistant to cleavage by the enzyme having 5' nuclease activity and the blocker portion is positioned to control the initial cleavage site or prevent the cleavage at a site or sites.

For example, to induce cleavage at the junction site between a hybridization portion of the PTO-SNV (3'-targeting portion) and a non-hybridization portion (5'-tagging portion), the 5'-end part of 3'-targeting portion of PTO-SNV may be blocked with blockers.

The number of blockers contained in the blocker portion may be not limited, preferably, 1-10, more preferably 2-10, still more preferably 3-8, most preferably 3-6 blockers. The blockers present in the PTO-SNV may be in a continuous or intermittent manner, preferably a continuous manner. The nucleotides as blockers with a backbone resistant to the 5' nuclease activity include any one known to one of skill in the art. For example, it includes various phosphorothioate linkages, phosphonate linkages, phosphoroamidate linkages and 2'-carbohydrates modifications. According to a more preferred embodiment, nucleotides having a backbone resistant to the 5' nuclease include phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-β-D-ribofuranosyl) modification.

According to an embodiment, a nucleotide as a blocker includes PNA (Peptide nucleic acid) or LNA (locked nucleic acid).

The term "part" used in conjunction with the PTO-SNV or CTO such as the part of the 5'-tagging portion of the PTO-SNV, the 5'-end part of the 3'-targeting portion of the PTO-SNV and the 5'-end part of the capturing portion of the CTO refers to a nucleotide sequence composed of 1-40, 1-30, 1-20, 1-15, 1-10 or 1-5 nucleotides, preferably 1, 2, 3 or 4 nucleotides.

According to an embodiment, the enzyme having the 5' nuclease activity is DNA polymerase having a 5' nuclease activity or FEN nuclease, more preferably a thermostable DNA polymerase having a 5' nuclease activity or FEN nuclease. A suitable DNA polymerase having a 5' nuclease activity in this invention is a thermostable DNA polymerase obtained from a variety of bacterial species, including *Thermus aquaticus* (Taq), *Thermus thermophilus* (Tth), *Thermus filiformis*, *Thermis flavus*, *Thermococcus literalis*, *Thermus antranikianii Thermus caldophilus*, *Thermus chliarophilus*, *Thermus flavus*, *Thermus igniterrae*, *Thermus lacteus*, *Thermus oshimai*, *Thermus ruber*, *Thermus rubens*, *Thermus scotoductus*, *Thermus silvanus*, *Thermus* species Z05, *Thermus* species sps 17, *Thermus thermophilus*, *Thermotoga maritima*, *Thermotoga neapolitana*, *Thermosipho africanus*, *Thermococcus litoralis; Thermococcus barossi*, *Thermococcus gorgonarius*, *Thermotoga maritima*, *Thermotoga neapolitana*, *Thermosipho africanus*, *Pyrococcus woesei*, *Pyrococcus horikoshii Pyrococcus abyssi*, *Pyrodictium occultum*, *Aquifex pyrophilus* and *Aquifex aeolieus*. Most preferably, the thermostable DNA polymerase is Taq polymerase.

Alternatively, the present invention may employ DNA polymerases having a 5' nuclease activity modified to have less polymerase activities.

The FEN (flap endonuclease) nuclease used is a 5' flap-specific nuclease.

The FEN nuclease suitable in the present invention comprises FEN nucleases obtained from a variety of bacterial species, including *Sulfolobus solfataricus*, *Pyrobaculum aerophilum*, *Thermococcus litoralis*, *Archaeaglobus venefi-cus*, *Archaeaglobus profundus*, *Acidianus brierlyi*, *Acidianus ambivalens*, *Desulfurococcus amylolyticus*, *Desulfurococcus mobilis*, *Pyrodictium brockii*, *Thermococcus gorgonarius*, *Thermococcus zilligii*, *Methanopyrus kandleri*, *Methanococcus igneus*, *Pyrococcus honkoshii*, *Aeropyrum pernix*, and *Archaeaglobus veneficus*.

Where the upstream primer is used in the step (a), it is preferable that the conditions for cleavage of the PTO-SNV comprise extension reaction of the upstream primer.

According to an embodiment, the upstream primer is used in the step (a), a template-dependent polymerase is used for extension of the upstream primer and the template-dependent polymerase is identical to the enzyme having the 5' nuclease activity.

Alternatively, the upstream primer is used in the step (a), a template-dependent polymerase is used for extension of the upstream primer and the template-dependent polymerase is different from the enzyme having the 5' nuclease activity.

The 5'-end part comprising the single nucleotide variation discrimination site may be composed of a hybridizable sequence with the target nucleic acid sequence. Alternatively, the 5'-end part may partially comprise a non-hybridizable sequence. The introduction of a non-hybridizable sequence into the 5'-end part is very advantageous over single strand formation of the 5'-end part when the PTO-SNV is hybridized with a different SNP allele from the SNP allele of interest having a SNP nucleotide non-complementary to the single nucleotide variation discrimination site.

According to an embodiment, the 5'-end part of the 3'-targeting portion of the PTO-SNV comprises a non-base pairing moiety located within 1-10 nucleotides (more particularly, 1-5 nucleotides) apart from the single nucleotide variation discrimination site.

The non-base pairing moiety prevents the 5'-end part of the 3'-targeting portion from formation of a double strand with the target nucleotide sequence when the PTO-SNV is hybridized with the target nucleic acid sequence having the SNP nucleotide non-complementary to the single nucleotide variation discrimination site.

According to an embodiment, the non-base pairing moiety does not inhibit the formation of a double strand between the 5'-end part and the target nucleic acid sequence when the PTO-SNV is hybridized with the target nucleic acid sequence having the SNP nucleotide complementary to the single nucleotide variation discrimination site.

According to an embodiment, the non-base pairing moiety enhances differentiation between the first initial cleavage site and the second initial cleavage site. For instance, where the cleavage sites do not become differentiated in the SNP allele of interest and different SNP alleles by difference in the single variation discrimination site due to no difference in hybridization patterns of the 5'-end part of the 3'-targeting portion of the PTO-SNV, the use of the non-base pairing moiety renders the hybridization patterns to become differentiated. In addition, even when the 5'-end part of the 3'-targeting portion of the PTO-SNV shows different hybridization patterns in the SNP allele of interest and different SNP alleles by difference in the single variation discrimination site, the use of the non-base pairing moiety enables to give much longer 3'-end portion of the second fragment than that of the first fragment, thereby completely preventing extension of the second fragment on the CTO.

The use of the non-base paring moiety improves the present method.

According to an embodiment, the use of the non-base pairing moiety (e.g., artificial mismatch nucleotide) enhances discrimination potential of the PTO-SNV to SNP nucleotides.

According to an embodiment, the differential recognition by the enzyme having the 5' nuclease activity between the first initial cleavage site and the second initial cleavage site is improved by the differentiation imposed by the non-base pairing moiety. The differentiation may be enhanced by the distance between the first initial cleavage site and the second initial cleavage site caused by the non-base pairing moiety. According to an embodiment, the non-base pairing moiety widens the distance between the first initial cleavage site and the second initial cleavage site.

According to an embodiment, the introduction of a non-base paring moiety sequence enables the second initial cleavage site to be adjusted.

According to an embodiment, the non-base pairing moiety is located downstream of the single nucleotide variation discrimination site.

For example, where a mismatch nucleotide as a non-base pairing moiety is introduced into a position 2 nucleotides apart, in a 3' direction, from the single nucleotide variation discrimination site, the second initial cleavage site is adjusted to a position 2 nucleotides apart from the single nucleotide variation discrimination site. In case of not using the mismatch nucleotide, the second initial cleavage site is positioned 1 nucleotide apart from the single nucleotide variation discrimination site. That is to say, the non-base pairing moiety may widen the distance between the first initial cleavage site and the second initial cleavage site.

The non-base pairing moiety includes any moieties not forming a base pair between target nucleic acid sequences. Particularly, the non-base pairing moiety is (i) a nucleotide comprising an artificial mismatch base, a non-base pairing base modified to be incapable of base pairing or a universal base, (ii) a non-base pairing nucleotide modified to be incapable of base pairing, or (iii) a non-base pairing chemical compound.

For example, the non-base pairing moiety includes alkylene group, ribofuranosyl naphthalene, deoxy ribofuranosyl naphthalene, metaphosphate, phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage and aryl phosphoroamidate linkage. Conventional carbon spacers are also used as non-base pairing moieties. Universal bases as non-base pairing moieties are useful in adjusting cleavage sites of the PTO-SNV.

As base pairs containing universal bases such as deoxyinosine, 1-(2'-deoxy-beta-D-ribofuranosyl)-3-nitropyrrole and 5-nitroindole have a lower binding strength than those between natural bases, universal bases may be employed as non-base pairing moieties under certain hybridization conditions.

The non-base pairing moiety introduced into the 5'-end part has particularly 1-5, more particularly 1-2 moieties. A plurality of non-base pairing moieties in the 5'-end part may be present in a consecutive or intermittent manner. Particularly, the non-base pairing moiety has 2-5 consecutive moieties.

Particularly, the non-base pairing moiety is a non-base pairing chemical compound.

According to an embodiment, the single nucleotide variation discrimination site and the non-base pairing moiety of the PTO-SNV are located within 10 nucleotides (more particularly 8 nucleotides, 7 nucleotides, 6 nucleotides, 5 nucleotides, 4 nucleotides, 3 nucleotides, 2 nucleotides or 1 nucleotide, still more particularly 1 nucleotide) apart from the 5'-end of the 3'-targeting portion.

Alternatively, the cleavage reaction may be executed only at the first initial cleavage site not at the second initial cleavage site. For instance, where an upstream probe is used and the cleavage reaction occurs at a site apart from a location site of the probe, the cleavage reaction may occur only at the first initial cleavage site when the PTO-SNV is hybridized with the SNP allele of interest. When the PTO-SNV is hybridized with different SNP alleles, the bifurcation site (the second initial cleavage site) may not be cleaved because of a long distance from the upstream probe.

According to an embodiment, where PTO-SNV is hybridized with different SNP alleles, the second initial cleavage site comprises an initial site of a double strand (i.e., bifurcation site) in structures including a single strand and a double strand.

Step (c): Hybridization of the Fragment Released from the PTO-SNV with CTO

The fragment released from the PTO-SNV is hybridized with a CTO (Capturing and Templating Oligonucleotide).

The CTO comprises in a 3' to 5' direction (i) a capturing portion comprising a nucleotide sequence complementary to the 5'-tagging portion or a part of the 5'-tagging portion of the PTO-SNV and (ii) a templating portion comprising a nucleotide sequence non-complementary to the 5'-tagging portion and the 3'-targeting portion of the PTO.

The templating portion may comprise any sequence so long as it is non-complementary to the 5'-tagging portion and the 3'-targeting portion of the PTO. Furthermore, the templating portion may comprise any sequence so long as it can be acted as a template for extension of the fragment released from the PTO.

The first fragment and the second fragment have commonly a hybridizable sequence with the capturing portion of the CTO and thus one of them is hybridized with the CTO.

The second fragment produced when hybridized with different SNP alleles comprises an additional 3'-end portion being different from the first fragment produced when hybridized with the SNP allele of interest.

According to an embodiment, the CTO has a sequence selected such that the CTO is not hybridized with the additional 3'-end portion of the second fragment to prevent the second fragment from extension when the second fragment is hybridized with the capturing portion of the CTO. For example, the sequence of the CTO may be selected such that the CTO has a mismatch nucleotide(s) opposed to the additional 3'-end portion of the second fragment. Alternatively, universal bases may be used instead of the mismatch nucleotide depending on reaction conditions.

The 3'-end of the CTO may comprise additional nucleotides not involved in hybridization with the fragment. Moreover, the capturing portion of the CTO may comprise a nucleotide sequence complementary only to a part of the fragment (e.g., a part of the fragment containing its 3'-end portion) so long as it is stably hybridized with the fragment.

The term used "capturing portion comprising a nucleotide sequence complementary to the 5'-tagging portion or a part of the 5'-tagging portion" is described herein to encompass various designs and compositions of the capturing portion of the CTO as discussed above.

The CTO may be designed to have a hairpin structure.

The length of the CTO may be widely varied. For example, the CTO is 7-1000 nucleotides, 7-500 nucleotides, 7-300 nucleotides, 7-100 nucleotides, 7-80 nucleotides, 7-60 nucleotides, 7-40 nucleotides, 15-1000 nucleotides, 15-500 nucleotides, 15-300 nucleotides, 15-100 nucleotides, 15-80 nucleotides, 15-60 nucleotides, 15-40 nucleotides, 20-1000 nucleotides, 20-500 nucleotides, 20-300 nucleotides, 20-100 nucleotides, 20-80 nucleotides, 20-60 nucleotides, 20-40 nucleotides, 30-1000 nucleotides, 30-500 nucleotides, 30-300 nucleotides, 30-100 nucleotides, 30-80 nucleotides, 30-60 nucleotides or 30-40 nucleotides in length. The capturing portion of the CTO may have any length so long as it is specifically hybridized with the fragment released from the PTO. For example, the capturing portion of the CTO is 5-100 nucleotides, 5-60 nucleotides, 5-40 nucleotides, 5-30 nucleotides, 5-20 nucleotides, 10-100 nucleotides, 10-60 nucleotides, 10-40 nucleotides, 10-30 nucleotides, 10-20 nucleotides, 15-100 nucleotides, 15-60 nucleotides, 15-40 nucleotides, 15-30 nucleotides or 15-20 nucleotides in length. The templating portion of the CTO may have any length so long as it can act as a template in extension of the fragment released from the PTO-SNV. For example, the templating portion of the CTO is 1-900 nucleotides, 1-400 nucleotides, 1-300 nucleotides, 1-100 nucleotides, 1-80 nucleotides, 1-60 nucleotides, 1-40 nucleotides, 1-20 nucleotides, 2-900 nucleotides, 2-400 nucleotides, 2-300 nucleotides, 2-100 nucleotides, 2-80 nucleotides, 2-60 nucleotides, 2-40 nucleotides, 2-20 nucleotides, 5-900 nucleotides, 5-400 nucleotides, 5-300 nucleotides, 5-100 nucleotides, 5-80 nucleotides, 5-60 nucleotides, 5-40 nucleotides, 5-30 nucleotides, 10-900 nucleotides, 10-400 nucleotides, 10-300 nucleotides, 15-900 nucleotides, 15-100 nucleotides, 15-80 nucleotides, 15-60 nucleotides, 15-40 nucleotides or 15-20 nucleotides in length.

The 3'-end of the CTO may have a 3'-OH terminal. Preferably, the 3'-end of the CTO is blocked to prohibit its extension. The non-extendible blocking of the CTO may be achieved in accordance with conventional methods. For instance, the blocking may be performed by adding to the 3'-hydroxyl group of the last nucleotide of the CTO a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

The fragment released from the PTO-SNV is hybridized with the CTO, providing a form suitable in extension of the fragment. Although an undigested PTO-SNV is also hybridized with the capturing portion of the CTO through its 5'-tagging portion, its 3'-targeting portion is not hybridized to the CTO which prohibits the formation of an extended duplex.

The hybridization in the step (c) can be described in detail with referring to descriptions in the step (a).

The first initial cleavage site (or the second initial cleavage site) may not be fixed but rather multiple in a condition. For example, initial cleavage sites may be positioned in a 5' to 3' direction at an initial nucleotide of a double strand (i.e., bifurcation site) in structures including a single strand and a double strand and 1-2 nucleotides apart from the initial nucleotide. In such case, particularly, the sequence of the CTO is selected such that the shortest fragment released by the first initial cleavage is selectively extended in the present invention to generate the extended strand indicative of the presence of the SNP allele of interest.

Step (d): Extension of the Fragment

When the first fragment is hybridized with the capturing portion of the CTO, it is extended to form an extended strand comprising an extended sequence complementary to the templating portion of the CTO. When the second fragment is hybridized with the capturing portion of the CTO, it is not extended (see FIG. 3).

The term used herein "extended sequence" in conjunction with the extended strand means only a newly extended sequence which is a portion of the extended strand except the first fragment. The extended strand comprises the first fragment and the extended sequence.

In certain embodiment, the extended strand of the first fragment and the CTO form an extended duplex in the step (d).

The term used herein "extended duplex" means a duplex formed by extension reaction in which the first fragment hybridized with the capturing portion of the CTO is extended using the templating portion of the CTO as a template and the template-dependent nucleic acid polymerase.

The extended duplex has different $T_m$ value from that of the hybrid between the uncleaved PTO-SNV and the CTO. Particularly, the extended duplex has higher $T_m$ value than the hybrid between the uncleaved PTO-SNV and the CTO.

The $T_m$ value of the extended duplex is adjustable by (i) a sequence and/or length of the first fragment, (ii) a sequence and/or length of the CTO or (iii) the sequence and/or length of the first fragment and the sequence and/or length of the CTO. The adjustable $T_m$ value of the extended duplex may be employed to give a target signal indicative of the presence of the extended strand by melting the extended duplex in the step (e).

The term used herein "$T_m$" refers to a melting temperature at which half a population of double stranded nucleic acid molecules are dissociated to single-stranded molecules. The $T_m$ value is determined by length and G/C content of nucleotides hybridized. The $T_m$ value may be calculated by conventional methods such as Wallace rule (R. B. Wallace, et al., *Nucleic Acids Research*, 6:3543-3547(1979)) and nearest-neighbor method (SantaLucia J. Jr., et al., Biochemistry, 35:3555-3562(1996)); Sugimoto N., et al., *Nucleic Acids Res.*, 24:4501-4505(1996)).

According to an embodiment, the $T_m$ value refers to actual $T_m$ values under reaction conditions actually practiced.

The template-dependent nucleic acid polymerase used in the step (d) may include any nucleic acid polymerases, for example, Klenow fragment of *E. coli* DNA polymerase I, a thermostable nucleic acid polymerase and bacteriophage T7 DNA polymerase. Preferably, the polymerase is a thermostable DNA polymerase which may be obtained from a variety of bacterial species, including *Thermus aquaticus* (Taq), *Thermus thermophilus* (Tth), *Thermus filiformis, Thermis flavus, Thermococcus literalis, Thermus antranikianii Thermus caldophilus, Thermus chliarophilus, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Thermococcus litoralis, Thermococcus barossi, Thermococcus gorgonarius, Thermotoga maritima, Thermotoga neapolitana, Thermosipho africanus, Pyrococcus furiosus*(Pfu), *Pyrococcus woesei, Pyrococcus horikoshii Pyrococcus abyssi, Pyrodictium occultum, Aquifex pyrophilus* and *Aquifex aeolieus*. Most preferably, the template-dependent nucleic acid polymerase is Taq polymerase.

According to an embodiment, the enzyme having the 5' nuclease activity used in the step (b) is identical to the template-dependent nucleic acid polymerase used in the step (d). Particularly, the enzyme having the 5' nuclease activity used in the step (b), the template-dependent nucleic acid polymerase used for extension of the upstream primer and the template-dependent nucleic acid polymerase used in the step (d) are identical to one another.

Generally, the extension of primers may be controlled by hybridization between a 3'-end part of primers and a template. By adjusting primer sequences and reaction conditions (e.g. annealing temperature), the extension of primers having at their 3'-end part 1-3 mismatch nucleotides is allowable. Alternatively, the extension of primers may be allowable only when they have perfectly complementary sequence to target sequences.

According to an embodiment, the sequence of the CTO is selected that either the first fragment or the second fragment is selectively extended.

According to an embodiment, the extension of the fragment is carried out under conditions such that the extension does not occur even when a single mismatch is present at the 3'-end part of the fragment.

Step (e): Detection of Signal Indicating the Presence of the Extended Strand

The signal indicating the presence of the extended strand is detected after the extension reaction.

Where the SNP allele of interest exists, the signal indicating the presence of the extended strand becomes detectable. In contrast, in the case of the absence of SNP allele of interest, the signal indicating the presence of the extended strand is not detected. Furthermore, the signal shows higher intensity for the target nucleic acid sequence homozygous for the SNP allele of interest than that of the target nucleic acid sequence heterozygous for the SNP allele of interest. Theoretically, the target nucleic acid sequence homozygous for the SNP allele of interest has twice of the SNP allele of interest than the target nucleic acid sequence heterozygous, which is reflected on the intensity of the signal. The present inventors have found out that the difference in signal intensity is induced by difference of SNP genotypes. Such results are found to be reproducible and patternable.

Therefore, the present method allows for SNP genotyping by using only one allele-specific PTO-SNV by measuring the intensities as well as detecting the presence of the signal indicating the presence of the extended strand.

Detection of Extended Duplex

According to an embodiment, the detection in the step (e) is carried out in accordance with the PTOCE assay comprising melting analysis or the PTOCE comprising detection at a pre-determined temperature using signals from either the extended strand or the extended duplex between the extended strand and the CTO (see WO2012/096523).

According to an embodiment, the extended strand of the first fragment and the CTO form an extended duplex in the step (d); wherein the extended duplex has a $T_m$ value adjustable by (i) a sequence and/or length of the first fragment, (ii) a sequence and/or length of the CTO or (iii) the sequence and/or length of the first fragment and the sequence and/or length of the CTO; wherein the extended duplex provides a target signal by (i) at least one label linked to the first fragment and/or CTO, (ii) a label incorporated into the extended duplex during the extension reaction, (iii) at least one label linked to the first fragment and/or CTO and a label incorporated into the extended duplex during the extension reaction or (iv) intercalating label; and wherein the presence of the extended strand is detected by measuring the target signal from the extended duplex in accordance with a melting analysis or a hybridization analysis for the extended duplex.

According to an embodiment, the extended strand of the first fragment and the CTO form an extended duplex in the step (d); wherein the extended duplex has a $T_m$ value adjustable by (i) a sequence and/or length of the first fragment, (ii) a sequence and/or length of the CTO or (iii) the sequence and/or length of the first fragment and the sequence and/or length of the CTO; wherein the extended duplex provides a target signal by (i) at least one label linked to the first fragment and/or CTO, (ii) a label incorporated into the extended duplex during the extension reaction, (iii) at least one label linked to the first fragment and/or CTO and a label incorporated into the extended duplex during the extension reaction or (iv) intercalating label; and wherein the presence of the extended strand is detected by measuring the target signal from the extended duplex at a pre-determined temperature sufficient to maintain a double strand of the extended duplex.

Detection Using Signaling Oligonucleotide

According to an embodiment, the extended strand of the first fragment may be detected by using a signaling oligonucleotide (SO) as disclosed in WO 2013/115442.

The SO to be hybridized with the extended strand comprises a complementary sequence to the extended strand.

According to an embodiment, the SO comprises a complementary sequence to the extended sequence.

According to an embodiment, at least a portion of the SO comprises a complementary sequence to the extended sequence. The portion of the SO comprising a complementary sequence to the extended sequence is at least one, two, three, four, five or ten nucleotides in length.

When a portion of the SO is designed to comprise a complementary sequence to a portion of the extended sequence newly synthesized, the $T_m$ value of the hybridization resultant of the SO and the extended strand becomes different from that of the hybridization resultant of the SO and the undigested PTO-SNV. The difference in the $T_m$ values ensures to differentiate signals from the two hybridization resultants. For example, non-target signals may be excluded in a real-time detection by adjusting temperature for detection in considering $T_m$ values, or in a melting curve analysis by melting peaks.

The SO may comprise throughout its whole sequence a complementary sequence to the extended sequence. Alternatively, the SO may comprise a portion having a complementary sequence to the extended sequence. For instance, one portion of the SO may comprise a complementary sequence to the extended sequence and the other portion may comprise a complementary sequence to the fragment. Particularly, the SO comprises throughout its whole sequence a complementary sequence to the extended sequence.

The SO may have any length, for example, 5-100 nucleotides, 5-80 nucleotides, 5-60 nucleotides, 5-40 nucleotides, 5-20 nucleotides, 5-10 nucleotides, 10-100 nucleotides, 10-80 nucleotides, 10-60 nucleotides, 10-40 nucleotides, 10-30 nucleotides, 10-20 nucleotides, 15-100 nucleotides, 15-80 nucleotides, 15-60 nucleotides, 15-40 nucleotides, 15-30 nucleotides, 15-20 nucleotides, 20-100 nucleotides, 20-80 nucleotides, 20-60 nucleotides, 20-40 nucleotides or 20-30 nucleotides.

The SO may have a hairpin structure.

The 3'-end of the SO is blocked to prohibit its extension. Alternatively, the SO having a non-blocked 3'-OH end may be extended.

According to an embodiment, wherein the extended strand of the first fragment is detected by using a signaling oligonucleotide (SO); wherein the SO comprises a complementary sequence to the extended strand and at least one label; the SO provides a detectable signal by association with or dissociation from the extended strand.

The term "association with or dissociation from the extended strand" has the same meaning as the term "hybridization with or denaturation from the extended strand".

According to an embodiment, the detectable signal indicative of the presence of the target nucleic acid sequence is provided by (i) the label linked to the SO, (ii) a combination of the label linked to the SO and a label linked to the fragment from the PTO-SNV, (iii) a combination of the label linked to the SO and a label to be incorporated into the extended strand during the extension reaction of the step (d), or (iv) a combination of the label linked to the SO and an intercalating dye.

The labeling systems useful in this invention will be described in detail as follows:
(i) Single Label Linked to the SO The present invention may provide signal for formation of the extended strand indicating the presence of the target nucleotide variation by using SO with a single label.
(ii) Intrastrand Interactive-Dual Label Linked to SO According to an embodiment, the SO is labeled with an interactive dual label comprising a reporter molecule and a quencher molecule and the hybridization between the SO and the extended strand in the step (e) induces change in signal from the interactive dual label to provide the detectable signal. Prior to hybridization of the SO, the reporter molecule and the quencher molecule on the SO are conformationally adjacent to each other to allow the quencher molecule to quench the signal from the reporter molecule. Upon hybridization, the reporter molecule and the quencher molecule on the SO are conformationally separated to allow the quencher molecule to unquench the signal from the reporter molecule, causing changes in signals from the interactive dual label.

According to an embodiment of the present invention using SO with an interactive dual label, the first fragment released from the PTO-SNV hybridized with the target nucleic acid sequence is hybridized with the capturing portion of the CTO and extended to form the extended strand. Upon hybridization of the extended strand with the SO, the reporter molecule and the quencher molecule on the SO are conformationally separated to allow the quencher molecule to unquench the signal from the reporter molecule, giving rise to changes in signals from the interactive dual label (e.g., increase in signal from reporter molecules). The reporter molecule and the quencher molecule on the SO not involved in the hybridization are conformationally adjacent to each other to allow the quencher molecule to quench the signal from the reporter molecule.

(iii) Interstrand Interactive-Dual Label

In the embodiment using the interstrand interactive-dual label, the extended strand has one of an interactive dual label comprising a reporter molecule and a quencher molecule and the SO has the other of the interactive dual label.

A label linked to the SO may be either a reporter molecule or a quencher molecule, and a label to the fragment may be either a quencher molecule or a reporter molecule.

According to an embodiment, the SO comprises one label among a reporter molecule and a quencher molecule of an interactive dual label, and the templating portion of the CTO comprises a nucleotide having a first non-natural base; wherein the extension reaction in the step (d) is performed in the presence of a nucleotide having both a second non-natural base with a specific binding affinity to the first non-natural base and the other among the reporter molecule and the quencher molecule, thereby incorporating the label into the extended strand; wherein the hybridization between the SO and the extended strand induces change in signal from the interactive dual label to provide the detectable signal.

The term used herein "non-natural base" refers to derivatives of natural bases such as adenine (A), guanine (G), thymine (T), cytosine (C) and uracil (U), which are capable of forming hydrogen-bonding base pairs. The term used herein "non-natural base" includes bases having different base pairing patterns from natural bases as mother compounds, as described, for example, in U.S. Pat. Nos. 5,432,272, 5,965,364, 6,001,983, and 6,037,120. The base pairing between non-natural bases involves two or three hydrogen bonds as natural bases. The base pairing between non-natural bases is also formed in a specific manner. Specific examples of non-natural bases include the following bases in base pair combinations: iso-C/iso-G, iso-dC/iso-dG, K/X, H/J, and M/N (see U.S. Pat. No. 7,422,850).

According to an embodiment, the SO comprises one label among a reporter molecule and a quencher molecule of an interactive dual label, and the extension reaction in the step (d) is performed in the presence of a nucleotide having the other among the reporter molecule and the quencher molecule, thereby incorporating the label into the extended strand; wherein the hybridization between the SO and the extended strand induces change in signal from the interactive dual label to provide the detectable signal.

(iv) Interactive-Dual Label Using Two SOs

In the embodiment of the interactive-dual label using two SOs, the method of the present invention uses an additional SO comprising a complementary sequence to the extended strand, the two SOs are hybridized with the extended strand in an adjacent manner, the two SOs each comprises one label among a reporter molecule and a quencher molecule of an interactive dual label; and the hybridization between the two SOs and the extended strand induces change in signal from the interactive dual label to provide the detectable signal.

(v) FRET Label Using Intercalating Dyes

According to an embodiment, the SO comprises an acceptor of a FRET and the hybridization in the step (e) is preformed in the presence of an intercalating dye; wherein the hybridization between the SO and the extended strand induces change in signal from the acceptor of the SO to provide the detectable signal.

Exemplified intercalating dyes useful in this invention include SYBR™ Green I, PO-PRO™-1, BO-PRO™-1, SYTO™43, SYTO™44, SYTO™45, SYTOX™Blue, POPO™-1, POPO™-3, BOBO™-1, BOBO™-3, LO-PRO™-1, JO-PRO™-1, YO-PRO™1, TO-PRO™1, SYTO™11, SYTO™13, SYTO™15, SYTO™16, SYTO™20, SYTO™23, TOTO®-3, YOYO™3, GelStar™ and thiazole orange. The intercalating dyes intercalate specifically into double-stranded nucleic acid molecules to generate signals.

A label may be linked to the SO or the PTO-SNV by conventional methods. Particularly, it is linked to the SO or PTO-SNV through a spacer containing at least three carbon atoms (e.g., 3-carbon spacer, 6-carbon spacer or 12-carbon spacer).

The SO useful in the present invention includes any probes capable of providing signals dependent on hybridization, for example, Molecular Beacon™ (U.S. Pat. No. 5,925,517), Hybeacons™ (D. J. French, et al., Molecular and Cellular Probes (2001) 13, 363-374 and U.S. Pat. No. 7,348,141), Dual-labeled, self-quenched probe (U.S. Pat. No. 5,876,930), LUX™ (I. A. Nazarenko, et al. Nucleic Acids Res 2002, 30:2089-2095. and U.S. Pat. No. 7,537,886) and Hybridization probe (Bernard P S, et al., Clin Chem 2000, 46, 147-148 and Deepti Parashar et al., Indian J Med Res 124, review article October 2006 385-398).

According to an embodiment, detection using SO may be carried out in a real-time manner using labels proving signals detectable in a real-time fashion.

Alternatively, the detection using SO may be carried out by a melting analysis or hybridization analysis because the labels used in the present invention are capable of providing detectable signals during melting of the hybridization resultant or melting and hybridization of the hybridization resultant.

According to an embodiment, detection using SO may be carried out with SO immobilized in a solid substrate.

Detection Using Hybridizing Oligonucleotide

According to an embodiment, the extended strand of the first fragment is detected by using a HO (hybridizing oligonucleotide); wherein the HO comprises a hybridizing nucleotide sequence complementary to the CTO and at least one label; wherein the extension of the first fragment induces the cleavage of the HO by an enzyme having a 5' nuclease activity to generate a detectable signal from the label.

According to an embodiment, the HO is located downstream of the first fragment on the CTO.

According to an embodiment, the HO comprises a hybridizing nucleotide sequence complementary to the templating portion of the CTO.

According to an embodiment, the template-dependent nucleic acid polymerase used for the extension of the fragment has a 5' nuclease activity.

The length of the HO may be widely varied. For example, the HO is 5-100 nucleotides, 5-80 nucleotides, 5-60 nucleotides, 5-40 nucleotides, 5-20 nucleotides, 5-10 nucleotides, 10-100 nucleotides, 10-80 nucleotides, 10-60 nucleotides, 10-40 nucleotides, 10-30 nucleotides, 10-20 nucleotides, 15-100 nucleotides, 15-80 nucleotides, 15-60 nucleotides, 15-40 nucleotides, 15-30 nucleotides, 15-20 nucleotides, 20-100 nucleotides, 20-80 nucleotides, 20-60 nucleotides, 20-40 nucleotides or 20-30 nucleotides in length.

In an embodiment of this invention, the HO is blocked at its 3'-end to prohibit its extension.

Briefly, the labeling systems useful in this invention will be described as follows:

(i) Single Label Linked to the HO

The present invention may provide signal for formation of the extended strand indicating the presence of the target nucleotide variation by using HO with a single label.

In an embodiment, the single label used herein has to be capable of providing a different signal depending on its presence on a double strand or single strand (e.g. the HO and the fragment of HO).

According to an embodiment, it is necessary to detect signal at temperature to allow for hybridization between the HO and the CTO.

(ii) Interactive Dual Label Linked to the HO

According to an embodiment, the detectable signal is provided by an interactive dual label linked to the HO.

The first fragment released from the PTO-SNV is hybridized with the capturing portion of the CTO and the HO labeled with an interactive dual label comprising a reporter molecule and a quencher molecule is hybridized with the templating portion to of the CTO. The extension of the first fragment induces cleavage of the HO to separate the reporter molecule from the quencher molecule, thereby providing a signal indicating the presence of the extended strand.

In such embodiment, where the dual label-linked nucleotides are relatively adjacent to each other, signal changes between before and after the HO cleavage may be utilized for signal detection.

Where the dual label-linked nucleotides are relatively distal to each other, the hybridization between the HO and the CTO induces conformational separation of the interactive dual label to unquench the signal from the reporter molecule even with no HO cleavage, thereby generating a signal change. In this case, the signal from a cleaved fragment of the HO may be detected at higher temperatures (e.g., 95° C.) to allow for prevention of hybridization between the HO and the CTO.

According to an embodiment, the reporter molecule and the quencher molecule may be located at any site on the HO, so long as the cleaved HO and the uncleaved HO can provide discriminative signals.

In certain embodiment, the reporter molecule and the quencher molecule each is located at both ends of the HO.

(iii) Interactive Dual Label Linked to the HO and the CTO

According to an embodiment, the detectable signal is provided by one of an interactive dual label comprising a reporter molecule and a quencher molecule linked to the HO and the other linked to the CTO.

In certain embodiment, the reporter molecule and the quencher molecule are positioned on the HO and the CTO such that a signal from the reporter molecule is quenched by the quencher molecule when the HO is hybridized to CTO. The cleavage of the HO induced by extension of the first fragment allows to release the HO from the CTO and separate the reporter molecule from the quencher molecule and then the quencher molecule to unquench the signal from the reporter molecule, thereby providing a signal indicating the presence of the extended strand.

According to an embodiment, it is necessary to detect signal at temperatures to allow for hybridization between the HO and the CTO.

In an embodiment, the HO may be designed to have a hairpin structure.

In certain embodiment, one of the reporter molecule and the quencher molecule is linked to the 3'-end of the HO and the other is linked to the 5'-end of the CTO.

According to an embodiment, the label system such as interactive-dual label using two HOs may be employed in the present method using HO. The interactive-dual label may be located at any site on the two HOs, so long as the cleaved HO and the uncleaved HO can provide discriminative signals. The types and locations of labels may be described with reference to descriptions for the SO.

According to an embodiment, the label system such as FRET label using intercalating dyes may be employed in the present method using HO. The FRET label may be located at any site on the HO, so long as the cleaved HO and the uncleaved HO can provide discriminative signals in the presence of the intercalating dye. The types and locations of labels may be described with reference to descriptions for the SO.

Alternatively, according to an embodiment, the extended strand of the first fragment is detected by using inhibition of the hybridization of the HO with the CTO even when the HO is not cleaved. The extended duplex formed by the extension of the first fragment can inhibit the hybridization of the HO with the CTO. The signal change depending on the hybridization or no hybridization of HO to CTO allows for determining the presence of the extended strand. According to an embodiment, the signals are provided by (i) a label linked to the HO, (ii) a label linked to the CTO, (iii) a label linked to the HO and a label linked to the CTO, or (iv) an intercalating label. The signal changes by occurrence or no occurrence of hybridization between the HO and the CTO, and labeling positions on the HO and the CTO can be described with reference to descriptions for the SO.

Detection by Size or Sequence of Extended Strand

According to an embodiment, the extended strand of the first fragment may be detected on the basis of either the size or sequence of the extended strand. For example, the extended strand can be detected by using an electrophoresis or a mass analysis (e.g., electron impact (EI), chemical ionization (CI), Field Desoption (FD), 252Cf-Plasma desoprtion (PD), desoprtion chemical ionization (DCI), secondary ion mass spectrometry (SIMS), fast atom bombardment (FAB), electrospray ionization (ESI), matrix-assisted laser desoprtion ionization (MALDI) and Tandem Mass Spectrometry).

Detection on a Solid Phase

According to an embodiment, the present invention is performed on the solid phase and an oligonucleotide (e.g. CTO, SO, HO or IO) is immobilized through its 5'-end or 3'-end onto a solid substrate. In a solid phase, the target signal provided on the solid substrate is measured.

Where the target signal is detected on the solid phase, an immobilized oligonucleotide (IO) with no label may be used instead of the SO. The descriptions for the SO can be applied to the IO corresponding to the SO with no label, except for descriptions for labels directly linked to the SO.

Where the IO is used, the extended strand may have a label for signal generation and detection. According to an embodiment, the label contained in the extended strand is (i) a single label linked to the fragment released from the PTO-SNV, (ii) a label to be incorporated into the extended strand during the extension reaction, or (iii) a combination of the single label linked to the fragment and the label to be incorporated into the extended strand during the extension reaction. Alternatively, where both the extended strand and the IO have no label, intercalating dyes such as SYBR™ Green I may be utilized.

The immobilization of the CTO, SO, HO or IO may be done in two fashions.

In the first fashion, the CTO, SO, HO or IO having been already immobilized on the solid substrate is involved in the reaction steps. In the second fashion, the CTO, SO, HO or IO is involved in a non-immobilized form then immobilized on the solid substrate during the reaction steps.

According to an embodiment, in the solid phase reaction, the single label is not required to possess the capability of generating signals different intensities depending on whether nucleic acid sequences having the single label is in a single strand or a double strand. The single label includes, but not limited to, a chemical label (e.g., biotin), an enzymatic label (e.g., alkaline phosphatase, peroxidase, β-galactosidase and β-glucosidase), a radioisotope label (e.g., $I^{125}$ and $C^{14}$), a fluorescent label, a luminescent label, a chemiluminescent label, and a metal label (e.g., gold).

For the solid phase reaction, the CTO, SO, HO or IO is immobilized directly or indirectly (preferably indirectly) through its 5'-end or 3'-end (preferably the 3'-end) onto the surface of the solid substrate. Furthermore, the CTO, SO, HO or IO may be immobilized on the surface of the solid substrate in a covalent or non-covalent manner. Where the immobilized oligonucleotides are immobilized indirectly onto the surface of the solid substrate, suitable linkers are used. The linkers useful in this invention may include any linkers utilized for probe immobilization on the surface of the solid substrate. For example, alkyl or aryl compounds with amine functionality, or alkyl or aryl compounds with thiol functionality serve as linkers for immobilization. In addition, poly (T) tail or poly (A) tail may serve as linkers and significantly decrease space hindrance that is an inhibitory factor to enzymatic actions (e.g., enzymatic cleavage reactions), contributing to increase in hybridization efficiency. The poly (T) tail or poly (A) tail as linkers is not considered a sequence of probes.

According to an embodiment, the CTO, SO, HO or IO may be immobilized on the solid substrate via interaction between binding partners (e.g., biotin/streptavidin). For example, the CTO, SO, HO or IO with one of binding partners (biotin and streptavidin) may be immobilized on the solid substrate whose surface is modified with the other binding partner.

According to an embodiment, the CTO, SO, HO or IO may be immobilized on the solid substrate by a nucleotide sequence for immobilization. For example, the solid substrate whose surface is modified with the nucleotide sequence for immobilization may be used to immobilize the CTO, SO, HO or IO with additional sequence complementary to the nucleotide sequence for immobilization.

According to an embodiment, the solid substrate used in the present invention is a microarray. The microarray to provide a reaction environment in this invention may include any those known to one of skill in the art. All processes of the present invention, i.e., hybridization to target nucleic acid sequences, cleavage, extension, melting and fluorescence detection, are carried out on the microarray. The immobilized oligonucleotides on the microarray serve as hybridizable array elements. The solid substrate to fabricate microarray includes, but not limited to, metals (e.g., gold, alloy of gold and copper, aluminum), metal oxide, glass, ceramic, quartz, silicon, semiconductor, Si/SiO$_2$ wafer, germanium, gallium arsenide, carbon, carbon nanotube, polymers (e.g., polystyrene, polyethylene, polypropylene and polyacrylamide), sepharose, agarose and colloids. The solid substrate may be in the form of a dipstick, a plate, a particle (e.g., bead), an affinity column and a membrane. A plurality of immobilized oligonucleotides in this invention may be immobilized on an addressable region or two or more addressable regions on a solid substrate that may comprise 2-1,000,000 addressable regions. Immobilized oligonucleotides may be fabricated to produce array or arrays for a given application by conventional fabrication technologies such as photolithography, ink-jetting, mechanical microspotting, and derivatives thereof.

The present invention performed on the solid phase can detect simultaneously a plurality of target nucleic acid sequences even using a single type of a label because the labels on the oligonucleotides immobilized are physically separated. In this regard, the number of target nucleic acid sequences to be detected by the present invention on the solid phase is not limited.

Using confocal detection devices, the signal only on the solid substrate may be detected without influence of labels suspended in a liquid phase.

The types of signal and numerical characteristics of signal intensity indicating the presence of the extended strand may be varied depending on types of labels and detecting methods.

The present method may use a wide variety of labels such as a fluorescent label, a luminescent label (e.g. bioluminescent, chemiluminescent, electrochemiluminescent), an electrochemical label, a metal label, chemical labels (e.g. biotin) and enzymatic labels (e.g. alkaline phosphatase, peroxidase, β-galactosidase and β-gluocosidase).

The detection of signal may be carried out in end-point manner or real-time manner. The signal may be used either with no further processing or with certain processing (e.g. melting analysis).

For example, the present method using a fluorescent label may detect a fluorescent signal from the label and measure intensity of the fluorescent signal after reactions. In such case, the type of the signal is fluorescence and the intensity of the signal is fluorescent intensity.

Where the present method using a fluorescent label employs Ct values as a real-time PCR analysis, the type of the signal is Ct or fluorescence and the intensity of the signal is Ct values.

In addition, the present method using a fluorescent label may detect a fluorescent signal from the label and produce a melting peak after processing fluorescent signals. In such case, the type of the signal is melting peaks and the intensity of the signal is the height or area of melting peaks.

According to an embodiment, the signal is a fluorescent signal provided from a fluorescent label and the intensity of the signal is the intensity of fluorescence of the fluorescent label. The intensity of fluorescence signal may be detected in a real-time manner or end-point manner.

As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent. The interactive label system includes a dual label based on "on contact-mediated quenching" (Salvatore et al., Nucleic Acids Research, 2002 (30) no. 21 e122 and Johansson et al., J. AM. CHEM. SOC 2002 (124) pp 6950-6956). The interactive label system includes any label system in which signal change is induced by interaction between at least two molecules (e.g. dye).

The reporter molecule and the quencher molecule useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), Dil (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red(615), Nile Red (628), YO-PRO™-3 (631), YOYO™-3 (631), R-phycocyanin (642), C-Phycocyanin (648), TO-PRO™-3 (660), TOTO3 (660), DiD DilC(5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. Preferably, the reporter molecule and the quencher molecule include JOE, FAM, TAMRA, ROX and fluorescein-based label.

Suitable fluorescence molecule and suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, 6th Edition (Molecular Probes, Eugene, Oreg., 1996) U.S. Pat. Nos. 3,996,345 and 4,351,760.

It is noteworthy that a non-fluorescent quencher molecule (e.g. black quencher or dark quencher) capable of quenching a fluorescence of a wide range of wavelengths or a specific wavelength may be used in the present invention.

In the signaling system comprising the reporter and quencher molecules, the reporter encompasses a donor of FRET and the quencher encompasses the other partner (acceptor) of FRET. For example, a fluorescein dye is used as the reporter and a rhodamine dye as the quencher.

The interactive dual label may be linked to one strand of a duplex. Where the strand containing the interactive dual label leaves in a single stranded state, it forms a hairpin or random coil structure to induce quenching between the interactive dual label. Where the strand forms a duplex, the quenching is relieved. Alternatively, where the interactive dual label is linked to nucleotides adjacently positioned on the strand, the quenching between the interactive dual label occurs. Where the strand forms a duplex and then is cleaved, the quenching becomes relieved.

Each of the interactive dual label may be linked to each of two strands of the duplex. The formation of the duplex induces quenching and denaturation of the duplex induces unquenching. Alternatively, where one of the two stands is cleaved, the unquenching may be induced.

Exemplified intercalating dyes useful in this invention include SYBR™ Green I, PO-PRO™-1, BO-PRO™-1, SYTO™43, SYTO™44, SYTO™45, SYTOX™Blue, POPO™-1, POPO™-3, BOBO™-1, BOBO™-3, LO-PRO™-1, JO-PRO™-1, YO-PRO™1, TO-PRO™1, SYTO™11, SYTO™13, SYTO™15, SYTO™16, SYTO™20, SYTO™23, TOTO™-3, YOYO™3, GelStar™ and thiazole orange. The intercalating dyes intercalate specifically into double-stranded nucleic acid molecules to generate signals.

Step (f): Determination of SNP Genotypes

Finally, a SNP genotype in the target nucleic acid sequence is determined by the intensity of the signal as well as the presence or absence of the signal detected in the step (e).

Where the signal shows the highest intensity, the target nucleic acid sequence is determined to be homozygous for the SNP allele of interest. Where the signal is not detected, the target nucleic acid sequence is determined to have no SNP allele of interest. Where the intensity of the signal is lower than that of the target nucleic acid sequence homozygous for the SNP allele of interest, the target nucleic acid sequence is determined to be heterozygous for the SNP allele of interest (see FIG. 4).

For example, where there is found two SNP nucleotides, G and A at a SNP site, the present method allows determining all of three SNP genotypes (i.e., GG, GA and AA) by use of only one allele-specific PTO-SNV in a SNP genotyping reaction. SNP Where the PTO-SNV comprises a single nucleotide variation discrimination site comprising a nucleotide (e.g, C) complementary to a SNP nucleotide (e.g, G) at a SNP site of the SNP allele of interest on the target nucleic acid, the signal intensity is detected to be the highest for the target nucleic acid sequence homozygous for the SNP allele of interest. Therefore, the target nucleic acid sequence to be analyzed is determined to have a genotype "GG". In the case that the signal intensity is detected to lower than that of the target nucleic acid sequence homozygous for the SNP allele of interest, the target nucleic acid sequence is determined to have a genotype "GA". Where the signal is not detected, the target nucleic acid sequence is determined to have a genotype "AA".

According to an embodiment of the present invention, a sample for SNP genotyping has a certain genotype of three SNP genotypes. Where nucleic acid molecules prepared from a sample are analyzed by using probes to be specifically hybridized with a first allele among two types of alleles including a first allele and a second allele, and signal intensities are measured, it would be theoretically appreciated that the intensity from a homozygote of the first allele is approximately two-fold higher than that from a heterozygote and the intensity from a homozygote of the second allele is zero.

According to an embodiment of the above-exemplified case, the intensity from the homozygote of the first allele is at least 1.3-fold, 1.4-fold, 1.5-fold, 1.6-fold, 1.7-fold or 1.8-fold higher than that from the heterozygote, and the intensity from the homozygote of the first allele is at most 2.7-fold, 2.6-fold, 2.5-fold, 2.4-fold, 2.3-fold or 2.2-fold lower than that from the heterozygote.

According to an embodiment of the above-exemplified case, the intensity from the homozygote of the second allele is at least 0.4-fold, 0.3-fold, 0.2-fold or 0.1-fold lower than that from the heterozygote.

According to an embodiment of the above-exemplified case, the intensity from the sample may be classified into three regions (high intensity region, medium intensity region and low intensity region) and SNP genotyping may be undertaken by determining which region of the three regions a signal is detected at.

In this regard, the present method allows for SNP genotyping by using only one allele-specific PTO-SNV in a single SNP genotyping reaction by measuring the intensities as well as the presence of the signal indicating the presence of the extended strand.

The conventional SNP genotyping methods were proposed to analyze only the presence or absence of signals (fluorescence or melting peak at certain $T_m$ value) indicating each allele. They had not suggested or taught SNP genotyping approaches by use of signal intensity. The present invention suggests a peculiar and practicable SNP genotyping for all alleles by use of measurements of not only the presence or absence of signals but also signal intensity for a single type of allele.

To our best knowledge, the present method firstly proposes a SNP genotyping method by using only one allele-specific oligonucleotide (i.e., PTO-SNV) in a single SNP genotyping reaction.

According to an embodiment, the present method is performed to detect a single SNP nucleotide of a plurality of SNP nucleotides found in the SNP.

According to an embodiment, the threshold values or ranges as reference values or ranges for determining SNP genotypes may be predetermined before performing the present method. The types of the threshold values include fluorescent signal intensity, $C_t$ value, and a height or area of the peak in a melting analysis or a hybridization analysis. The supply of the threshold values may be accompanied with information about reaction conditions such as concentrations of reagents, reaction time and reaction temperature.

According to an embodiment, the reactions for nucleic acid molecules of which genotypes are predetermined may be carried out to provide reference values for determining SNP genotypes.

According to an embodiment, a signal intensity value or range (threshold value or range) is determined for each SNP genotype using standard samples under certain conditions. Then, the SNP genotyping is performed from signal intensities of unknown samples obtained under the conditions with reference to the signal intensity value or range for each SNP genotype of standard samples. The conditions for determining the signal intensity value or range of the standard samples may be expressed as "standard conditions".

According to an embodiment, the difference in the signal intensity depending on SNP genotypes may remain even when the initial amounts of the target nucleic acid sequence are different. For example, the reaction conditions in batches are same except that the initial amounts of the target nucleic acid sequence are different. Such feature allows for SNP genotyping in a reliable and reproducible manner.

According to an embodiment, the extended strand may be further amplified by using a primer forming a pair of primers with the PTO-SNV fragment.

According to an embodiment, the method is performed to detect at least two types of SNPs; wherein the upstream oligonucleotide comprises at least two types of oligonucleotides and the PTO-SNV comprises at least two types of the PTO-SNVs.

According to an embodiment, the method is performed in the presence of a downstream primer.

The PTO-SNV and CTO may be comprised of naturally occurring dNMPs. Alternatively, the PTO-SNV and CTO may be comprised of modified nucleotide or non-natural nucleotide such as PNA (peptide nucleic acid, see PCT Publication No. WO 92/20702) and LNA (locked nucleic acid, see PCT Publication Nos. WO 98/22489, WO 98/39352 and WO 99/14226). The PTO-SNV and CTO may comprise universal bases such as deoxyinosine, inosine, 1-(2'-deoxy-beta-D-ribofuranosyl)-3-nitropyrrole and 5-nitroindole. The term "universal base" refers to one capable of forming base pairs with each of the natural DNA/RNA bases with little discrimination between them.

According to an embodiment, the method further comprises repeating all or some of the steps (a)-(e) with denaturation between repeating cycles. The reaction repetition is accompanied with amplification of the target nucleic acid sequence. Preferably, the amplification is performed in accordance with PCR (polymerase chain reaction) which is disclosed in U.S. Pat. Nos. 4,683,195, 4,683,202, and 4,800,159.

The denaturation may be carried out by conventional technologies, including, but not limited to, heating, alkali, formamide, urea and glycoxal treatment, enzymatic methods (e.g., helicase action), and binding proteins. For instance, the melting can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

According to an embodiment, the steps (a)-(e) are performed in a reaction vessel or in separate reaction vessels. For example, the steps (a)-(b), (c)-(d) or (e) may be performed in separate reaction vessels.

According to an embodiment, the steps (a)-(e) may be simultaneously or separately even in a reaction vessel depending on reaction conditions (particularly, temperature). For example the steps (a)-(b) and (c)-(e) may be simultaneously or separately even in a reaction vessel depending on reaction conditions (particularly, temperature).

The present invention does not require that target nucleic acid sequences to be detected and/or amplified have any particular sequence or length, including any DNA (gDNA and cDNA) and RNA molecules.

The target nucleic acid sequences which may be detected and/or amplified include any naturally occurring eukaryotic (for example, protozoans and parasites, fungi, yeast, higher plants, lower and higher animals, including mammals and humans) or viral (for example, human foamy virus, human T-lymphotropic virus, and HIV, etc.) or viroid nucleic acid.

The target nucleic acid sequence to be detected by the present invention includes a wide variety of nucleic acid sequences, e.g., sequences in a genome.

The sample for SNP genotyping includes polyploidy cells, particularly, diploid cells.

The present invention may be carried out simultaneously with amplification of a target nucleic acid sequence using a primer pair composed of an upstream primer and a downstream primer capable of synthesizing the target nucleic acid sequence.

In another aspect of this invention, there is provided a method for determining a SNP (single nucleotide polymorphism) genotype, comprising:

(a) hybridizing a target nucleic acid sequence containing a SNP with a primer pair comprising an upstream primer and an downstream primer and a PTO-SNV (Probing and Tagging Oligonucleotide for Single Nucleotide Variation); wherein the upstream primer and the downstream primer comprise a hybridizing nucleotide sequence complementary to the target nucleic acid sequence; the PTO-SNV comprises (i) a 3'-targeting portion comprising a hybridizing nucleotide sequence complementary to the target nucleic acid sequence, (ii) a 5'-tagging portion comprising a nucleotide sequence non-complementary to the target nucleic acid sequence, and (iii) a single nucleotide variation discrimination site comprising a nucleotide complementary to a SNP nucleotide at a SNP site of the SNP allele of interest on the target nucleic acid sequence, positioned on a 5'-end part of the 3'-targeting portion; wherein the 3'-targeting portion is hybridized with the target nucleic acid sequence and the 5'-tagging portion is not hybridized with the target nucleic acid sequence; the PTO-SNV is located between the upstream primer and the downstream primer; wherein the PTO-SNV is blocked at its 3'-end to prohibit its extension;

(b) contacting the resultant of the step (a) to a template-dependent nucleic acid polymerase having a 5' nuclease activity under conditions for extension of the primers and for cleavage of the PTO-SNV; wherein when the PTO-SNV is hybridized with the SNP allele of interest having the SNP nucleotide complementary to the single nucleotide variation discrimination site, the 5'-end part of the 3'-targeting portion forms a double strand with the target nucleic acid sequence to induce cleavage from a first initial cleavage site, and a first fragment is released; wherein when the PTO-SNV is hybridized with a different SNP allele from the SNP allele of interest having a SNP nucleotide non-complementary to the single nucleotide variation discrimination site, the 5'-end part of the 3'-targeting portion does not form a double strand with the target nucleic acid sequence to induce cleavage from a second initial cleavage site located downstream of the first initial cleavage site, and a second fragment is released; wherein the second fragment comprises an additional 3'-end portion allowing the second fragment different from the first fragment;

(c) hybridizing the fragment released from the PTO-SNV with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO-SNV and (ii) a templating portion comprising a nucleotide sequence non-complementary to the 5'-tagging portion and the 3'-targeting portion of the PTO-SNV; wherein the first fragment or the second fragment released from the PTO-SNV is hybridized with the capturing portion of the CTO;

(d) performing an extension reaction using the resultant of the step (c) and a template-dependent nucleic acid polymerase; wherein when the first fragment is hybridized with the capturing portion of the CTO, it is extended to form an extended strand comprising an extended sequence complementary to the templating portion of the CTO; wherein when the second fragment is hybridized with the capturing portion of the CTO, it is not extended;

(e) detecting a signal indicating the presence of the extended strand; wherein the signal shows higher intensity for the target nucleic acid sequence homozygous for the SNP allele of interest than that of the target nucleic acid sequence heterozygous for the SNP allele of interest, and the signal is not provided from the target nucleic acid sequence having no SNP allele of interest; and (f) determining a SNP genotype in the target nucleic acid sequence by the intensity of the signal detected in the step (e).

Since the present invention simultaneously with amplification of a target nucleic acid sequence follows the steps of the present method described above, the common descriptions between them are omitted in order to avoid undue redundancy leading to the complexity of this specification.

According to an embodiment, the method further comprises repeating all or some of the steps (a)-(e) with denaturation between repeating cycles. The reaction repetition is accompanied with amplification of the target nucleic acid sequence. Preferably, the amplification is performed in accordance with PCR (polymerase chain reaction) which is disclosed in U.S. Pat. Nos. 4,683,195, 4,683,202, and 4,800,159.

According to an embodiment, the present invention may be performed with no help of upstream oligonucleotides. In such case, conventional enzymes having upstream oligonucleotide-independent 5' nuclease activity may be used. Among template-dependent polymerases having 5' nuclease activity, there are several enzymes having upstream oligonucleotide-independent 5' nuclease activity, e.g., Taq DNA polymerase.

Considering amplification of target nucleic acid sequences, reaction conditions and 5' nuclease activity, the present invention is advantageously performed using upstream oligonucleotides.

The method for determining a SNP genotype based on upstream oligonucleotide-independent 5' nuclease activity comprises:

(a) hybridizing a target nucleic acid sequence containing a SNP with a PTO-SNV (Probing and Tagging Oligonucleotide for Single Nucleotide Variation); wherein the PTO-SNV comprises (i) a 3'-targeting portion comprising a hybridizing nucleotide sequence complementary to the target nucleic acid sequence, (ii) a 5'-tagging portion comprising a nucleotide sequence non-complementary to the target nucleic acid sequence, and (iii) a single nucleotide variation discrimination site comprising a nucleotide complementary to a SNP nucleotide at a SNP site of the SNP allele of interest on the target nucleic acid sequence, positioned on a 5'-end part of the 3'-targeting portion; wherein the 3'-targeting portion is hybridized with the target nucleic acid sequence and the 5'-tagging portion is not hybridized with the target nucleic acid sequence;

(b) contacting the resultant of the step (a) to an enzyme having a 5' nuclease activity under conditions for cleavage of the PTO-SNV; wherein when the PTO-SNV is hybridized with the SNP allele of interest having the SNP nucleotide complementary to the single nucleotide variation discrimination site, the 5'-end part of the 3'-targeting portion forms a double strand with the target nucleic acid sequence to induce cleavage from a first initial cleavage site, and a first fragment is released; wherein when the PTO-SNV is hybridized with a different SNP allele from the SNP allele of interest having a SNP nucleotide non-complementary to the single nucleotide variation discrimination site, the 5'-end part of the 3'-targeting portion does not form a double strand with the target nucleic acid sequence to induce cleavage from a second initial cleavage site located downstream of the first initial cleavage site, and a second fragment is released; wherein the second fragment comprises an additional 3'-end portion allowing the second fragment different from the first fragment;

(c) hybridizing the fragment released from the PTO-SNV with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO-SNV and (ii) a templating portion comprising a nucleotide sequence non-complementary to the 5'-tagging portion and the 3'-targeting portion of the PTO-SNV; wherein the first fragment or the second fragment released from the PTO-SNV is hybridized with the capturing portion of the CTO;

(d) performing an extension reaction using the resultant of the step (c) and a template-dependent nucleic acid polymerase; wherein when the first fragment is hybridized with the capturing portion of the CTO, it is extended to form an extended strand comprising an extended sequence complementary to the templating portion of the CTO; wherein when the second fragment is hybridized with the capturing portion of the CTO, it is not extended;

(e) detecting a signal indicating the presence of the extended strand; wherein the signal shows higher intensity for the target nucleic acid sequence homozygous for the SNP allele of interest than that of the target nucleic acid sequence heterozygous for the SNP allele of interest, and the signal is not provided from the target nucleic acid sequence having no SNP allele of interest; and (f) determining a SNP genotype in the target nucleic acid sequence by the intensity of the signal detected in the step (e).

Since the present method based on upstream oligonucleotide-independent 5' nuclease activity is the same as those using upstream oligonucleotides except for no use of upstream oligonucleotides, the common descriptions between them are omitted in order to avoid undue redundancy leading to the complexity of this specification.

In another aspect of this invention, there is a kit for determining a SNP (single nucleotide polymorphism) genotype, comprising:

(a) PTO-SNV (Probing and Tagging Oligonucleotide for Single Nucleotide Variation); wherein the PTO-SNV comprises (i) a 3'-targeting portion comprising a hybridizing nucleotide sequence complementary to the target nucleic acid sequence, (ii) a 5'-tagging portion comprising a nucleotide sequence non-complementary to the target nucleic acid sequence, and (iii) a single nucleotide variation discrimination site comprising a nucleotide complementary to a SNP nucleotide at a SNP site of the SNP allele of interest on the target nucleic acid sequence, positioned on a 5'-end part of the 3'-targeting portion; wherein the 3'-targeting portion is hybridized with the target nucleic acid sequence and the 5'-tagging portion is not hybridized with the target nucleic acid sequence;

(b) an upstream oligonucleotide; wherein the upstream oligonucleotide comprises a hybridizing nucleotide sequence complementary to the target nucleic acid sequence; wherein the upstream oligonucleotide is located upstream of the PTO-SNV; the upstream oligonucleotide or its extended strand induces cleavage of the PTO-NV by an enzyme having a 5' nuclease activity; and (c) a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO-SNV and (ii) a templating portion comprising a nucleotide sequence non-complementary to the 5'-tagging portion and the 3'-targeting portion of the PTO-SNV; wherein a first fragment or a second fragment released from the PTO-SNV is hybridized with the capturing portion of the CTO; and (d) an instruction that describes the method of the present invention.

Since the kits of this invention are prepared to perform the present methods, the common descriptions between them are omitted in order to avoid undue redundancy leading to the complexity of this specification.

According to an embodiment, the kit further comprises the enzyme having the 5' nuclease activity, a template-dependent nucleic acid polymerase or their combination.

According to an embodiment, the kit further comprises SO, HO, IO or a label to be incorporated.

Optionally, the kits described hereinabove may optionally include the reagents required for performing target amplification PCR reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The components of the kit may be present in separate containers, or multiple components may be present in a single container.

The instructions for describing or practicing the methods of the present invention may be recorded on a suitable recording medium. For example, the instructions may be printed on a substrate, such as paper and plastic. In other embodiments, the instructions may be present as an electronic storage data file present on a suitable computer readable storage medium such as CD-ROM and diskette. In yet other embodiments, the actual instructions may not be present in the kit, but means for obtaining the instructions from a remote source, e.g. via the internet, are provided. An example of this embodiment is a kit that includes a web address where the instructions can be viewed and/or from which the instructions can be downloaded.

The features and advantages of this invention will be summarized as follows:

(a) Where SNP genotyping is carried out simultaneously for a plurality of SNPs in a sample (i.e., multiplex SNP genotyping), the conventional technologies should generate distinct signals for all alleles for all SNPs. Therefore, the conventional methods are very likely to be encountered with limitations in the number of SNPs for multiplex SNP genotyping. In contrast, the present method allows multiplex SNP genotyping for a relatively large number of SNPs because it can determine SNP genotypes by detection of only one allele.

(b) The present invention can be performed using a multitude of labeling systems. For example, the labels linked to any site of PTO-SNV, CTO, SO, and/or HO can be utilized for providing the target signal indicating the extended strand. Also, labels incorporated into the extended duplex during the extension reaction can be used in the present invention. In addition to this, a combination of such labels can be used. The versatile labeling systems applicable to the present invention allow us to choose a proper labeling system depending on experimental conditions or objectives.

(c) It is noteworthy that the sequence of the 5'-tagging portion of PTO-SNV and the sequence of CTO can be selected with no consideration of target nucleic acid sequences. This makes it possible to pre-design a pool of sequences for the 5'-tagging portion of PTO-SNV and CTO. Although the 3'-targeting portion of the PTO-SNV has to be prepared with considering target nucleic acid sequences, the CTO can be prepared in a ready-made fashion with no consideration or knowledge of target nucleic acid sequences. Such features provide prominent advantages in multiple target detection, inter alia, on a microarray assay using CTOs immobilized onto a solid substrate.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Evaluation of Allelic Discrimination of Single Nucleotide Polymorphism (SNP) Using Single Type of PTO-SNV We examined whether the method using a single type of PTO-SNV is capable of genotyping a single nucleotide polymorphism (SNP) of a target nucleic acid sequence.

The present method for SNP genotyping permits SNP genotyping of two or more alleles by detecting only a single allele. For example, where the PTO-SNV specific to a mutant allele is used, the present method finally provides the signal for nucleic acid sequences homozygous or heterozygous for the mutant allele. Because the nucleic acid sequence homozygous for the mutant allele has different mutant allele ratio from that heterozygous for the mutant allele, the amounts of the extension strand produced are different from each other. The intensity of the signal finally detected is proportional to the amount of the extension strand, and therefore the mutant homozygote shows higher signal intensity than mutant heterozygote. The difference in the signal intensity ensures to differentiate mutant homozygote from mutant heterozygote. The wild-type homozygote does not provide the signal.

Taq DNA polymerase having a 5' nuclease activity was used for the extension of the upstream primer and downstream primer, the cleavage of PTO-SNV and the extension of PTO-SNV fragment. PTO-SNV and CTO are blocked with a carbon spacer at their 3'-ends. MTHFR C677T wild-type homozygous (CC), heterozygous (CT) and mutant homozygous (TT) human genomic DNAs were used as target DNAs.

PTO-SNV has no label. The single nucleotide variation discrimination site of PTO-SNV has a nucleotide (A) complementary to the SNP nucleotide (T) of mutant allele of MTHFR C677T. (SEQ ID NO: 3).

In this Example, the presence of the extended strand produced depending on the presence of the mutant (T) allele of MTHFR C677T was detected by melting analysis of the extended duplex formed with the extended strand and CTO. Different melting peak heights will be obtained depending on the allelic composition of MTHFR C677T in the target DNA (i.e., wild-type homozygote (CC); heterozygote (CT); and mutant homozygote (TT)).

CTO is labeled with a quencher molecule (BHQ-2) and a fluorescent reporter molecule (CAL Fluor Red 610) in its templating portion. (SEQ ID NO: 4)

The sequences of upstream primer, downstream primer, PTO-SNV and CTO used in this Example are:

```
MTHFR-F
                                                   (SEQ ID NO: 1)
5'-GCAGGGAGCTTTGAGGCTGIIIIIAAGCACTTGA-3'

MTHFR-R
                                                   (SEQ ID NO: 2)
5'-CCTCACCTGGATGGGAAAGATIIIIIGGACGATGG-3'

MTHFR-PTO-SNV
                                                   (SEQ ID NO: 3)
5'-CTCCTGCTCGCGTACTCCCGCAGACACCTTCTCCTTCAAG
[Spacer C3]-3'

MTHFR-CTO
                                                   (SEQ ID NO: 4)
5'-[BHQ-2]TTTTTTTTTTTTTTTTTTT[T(Cal Fluor Red
610)]CTTATACGCGAGCAGGAG[Spacer C3]-3'
(I: Deoxyinosine)
(Underlined letters indicate the 5'-tagging portion of PTO-
SNV)
(Bold letter indicates the single nucleotide variation dis-
crimination site)
```

The reaction was conducted in the final volume of 20 μl containing 100 ng of MTHFR C677T wild-type homozygous (CC), heterozygous (CT) or mutant homozygous (TT) human genomic DNAs, 10 pmole of upstream primer (SEQ ID NO: 2), 10 pmole of downstream primer (SEQ ID NO: 1), 2 pmole of PTO-SNV (SEQ ID NO: 3) and 1 pmole of CTO (SEQ ID NO: 4), and 10 μl of 2× Master Mix containing 2.5 mM $MgCl_2$, 200 μM of dNTPs and 1.6 units of Taq DNA polymerase (Solgent, Korea); the tube containing the reaction mixture was placed in the real-time thermocycler (CFX96, Bio-Rad); the reaction mixture was denatured for 15 min at 95° C. and subjected to 50 cycles of 30 sec at 95° C., 60 sec at 60° C., 30 sec at 72° C. After the reaction, a melting curve was obtained by cooling the reaction mixture to 55° C., holding at 55° C. for 30 sec, and heating slowly at 55° C. to 85° C. The fluorescence was measured continuously during the temperature rise to monitor dissociation of double-stranded DNAs. A melting peak was derived from the melting curve data.

Figure 4:
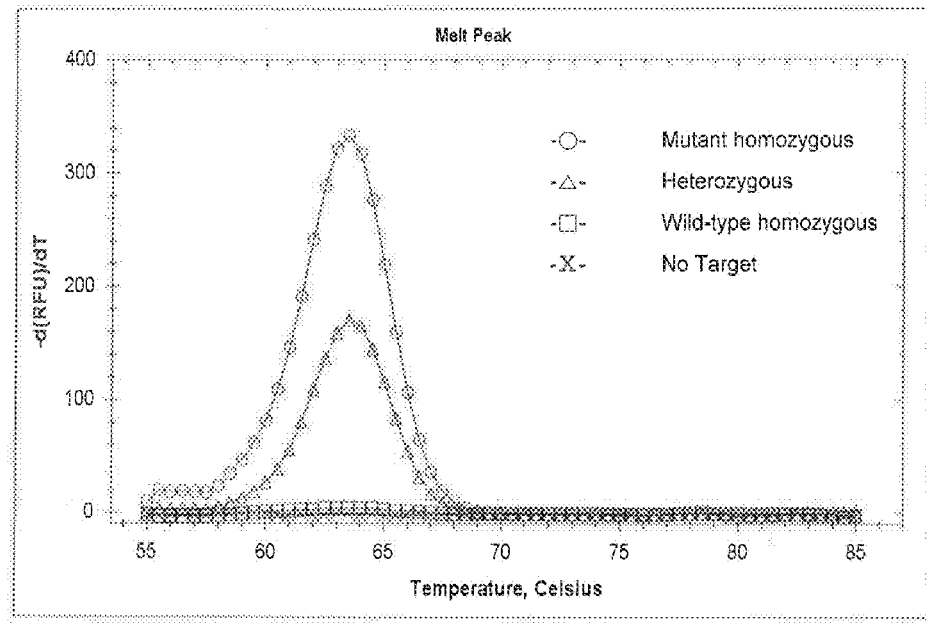
FIG. 4 shows the results of allelic discrimination of SNP in the MTHFR (Methylenetetrahydrofolate reductase) gene by the present method.

As shown in FIG. 4, the peaks corresponding to the expected Tm value of the extended duplexes were detected in the presence of mutant homozygous (TT) and heterozygous (CT) DNA. The peak height of heterozygous (CT) DNA was roughly half of mutant homozygous (TT) DNA. No peak was detected in the presence of wild-type homozygous (CC) DNA. No peak was detected in the absence of the target DNAs.

This results show that different SNP genotypes provide distinguishable signal intensities (e.g. melting peak heights) in the method using single type of PTO-SNV, which allows the allelic discrimination of SNP.

Having described a preferred embodiment of the present invention, it is to be understood that variants and modifications thereof falling within the spirit of the invention may become apparent to those skilled in this art, and the scope of this invention is to be determined by appended claims and their equivalents.

---

What is claimed is:

1. A method for determining a SNP (single nucleotide polymorphism) genotype, comprising:
   (a) hybridizing a target nucleic acid sequence containing a SNP with an upstream oligonucleotide and a PTO-SNV (Probing and Tagging Oligonucleotide for Single Nucleotide Variation); wherein the upstream oligonucleotide comprises a hybridizing nucleotide sequence complementary to the target nucleic acid sequence; the PTO-SNV comprises (i) a 3'-targeting portion comprising a hybridizing nucleotide sequence complementary to the target nucleic acid sequence, (ii) a 5'-tagging portion comprising a nucleotide sequence non-complementary to the target nucleic acid sequence, and (iii) a single nucleotide variation discrimination site comprising a nucleotide complementary to a SNP nucleotide at a SNP site of the SNP allele of interest on the target nucleic acid sequence, positioned on a 5'-end part of the 3'-targeting portion; wherein the 3'-targeting portion is hybridized with the target nucleic acid sequence and the 5'-tagging portion is not hybridized with the target nucleic acid sequence; the upstream oligonucleotide is located upstream of the PTO-SNV; the upstream oligonucleotide or its extended strand induces cleavage of the PTO-SNV by an enzyme having a 5' nuclease activity;
   (b) contacting the resultant of the step (a) to an enzyme having a 5' nuclease activity under conditions for cleavage of the PTO-SNV; wherein when the PTO-SNV is hybridized with the SNP allele of interest having the SNP nucleotide complementary to the single nucleotide variation discrimination site, the 5'-end part of the 3'-targeting portion forms a double strand with the target nucleic acid sequence to induce cleavage from a first initial cleavage site, and a first fragment is released; wherein when the PTO-SNV is hybridized with a different SNP allele from the SNP allele of interest having a SNP nucleotide non-complementary to the single nucleotide variation discrimination site, the 5'-end part of the 3'-targeting portion does not form a double strand with target nucleic acid sequence to induce cleavage from a second initial cleavage site located downstream of the first initial cleavage site, and a second fragment is released; wherein the second fragment comprises an additional 3'-end portion allowing the second fragment different from the first fragment;
   (c) hybridizing the fragment released from the PTO-SNV with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO-SNV and (ii) a templating portion comprising a nucleotide sequence non-complementary to the 5'-tagging portion and the 3'-targeting portion of the PTO-SNV; wherein the first fragment or the second fragment released from the PTO-SNV is hybridized with the capturing portion of the CTO;
   (d) performing an extension reaction using the resultant of the step (c) and a template-dependent nucleic acid polymerase; wherein when the first fragment is hybridized with the capturing portion of the CTO, it is extended to form an extended strand comprising an extended sequence complementary to the templating portion of the CTO; wherein when the second fragment is hybridized with the capturing portion of the CTO, it is not extended;
   (e) detecting a signal indicating the presence of the extended strand; wherein the signal shows higher intensity for the target nucleic acid sequence homozygous for the SNP allele of interest than that of the target nucleic acid sequence heterozygous for the SNP allele of interest, and the signal is not provided from the target nucleic acid sequence having no SNP allele of interest; and
   (f) determining a SNP genotype in the target nucleic acid sequence by the intensity of the signal detected in the step (e).

2. The method according to claim 1, wherein the CTO has a sequence selected such that the CTO is not hybridized with the additional 3'-end portion of the second fragment to prevent the second fragment from extension when the second fragment is hybridized with the capturing portion of the CTO.

3. The method according to claim 1, wherein the single nucleotide variation discrimination site is located within 10 nucleotides apart from the 5'-end of the 3'-targeting portion of the PTO-SNV.

4. The method according to claim 1, wherein the 5'-end part of the 3'-targeting portion of the PTO-SNV comprises a non-base pairing moiety located within 1-5 nucleotides apart from the single nucleotide variation discrimination site; wherein the non-base pairing moiety enhances differentiation between the first initial cleavage site and the second initial cleavage site.

5. The method according to claim 4, wherein the non-base pairing moiety is (i) a nucleotide comprising an artificial mismatch base, a non-base pairing base modified to be incapable of base pairing or a universal base, (ii) a non-base pairing nucleotide modified to be incapable of base pairing, or (iii) a non-base pairing chemical compound.

6. The method according to claim 1, wherein the extended strand of the first fragment and the CTO form an extended duplex in the step (d); wherein the extended duplex has a $T_m$ value adjustable by (i) a sequence and/or length of the first fragment, (ii) a sequence and/or length of the CTO or (iii) the sequence and/or length of the first fragment and the sequence and/or length of the CTO; wherein the extended duplex provides the signal by (i) at least one label linked to the first fragment and/or CTO, (ii) a label incorporated into the extended duplex during the extension reaction, (iii) at least one label linked to the first fragment and/or CTO and a label incorporated into the extended duplex during the extension reaction or (iv) intercalating label; and wherein the presence of the extended strand is detected by measuring the signal from the extended duplex in accordance with a melting analysis or a hybridization analysis for the extended duplex.

7. The method according to claim 1, wherein the extended strand of the first fragment and the CTO form an extended duplex in the step (d); wherein the extended duplex has a $T_m$ value adjustable by (i) a sequence and/or length of the first fragment, (ii) a sequence and/or length of the CTO or (iii) the sequence and/or length of the first fragment and the sequence and/or length of the CTO; wherein the extended duplex provides the signal by (i) at least one label linked to the first fragment and/or CTO, (ii) a label incorporated into the extended duplex during the extension reaction, (iii) at least one label linked to the first fragment and/or CTO and a label incorporated into the extended duplex during the extension reaction or (iv) intercalating label; and wherein the presence of the extended strand is detected by measuring the signal from the extended duplex at a pre-determined temperature sufficient to maintain a double strand of the extended duplex.

8. The method according to claim 1, wherein the extended strand of the first fragment is detected by using a signaling oligonucleotide (SO); wherein the SO comprises a complementary sequence to the extended strand and at least one label; the SO provides the signal by association with or dissociation from the extended strand.

9. The method according to claim 8, wherein the signal is provided by (i) the label linked to the SO, (ii) a combination of the label linked to the SO and a label linked to the first fragment, (iii) a combination of the label linked to the SO and a label to be incorporated into the extended strand during the extension reaction of the step (d), or (iv) a combination of the label linked to the SO and an intercalating dye.

10. The method according to claim 8, wherein the method uses an additional SO comprising a complementary sequence to the extended strand, the two SOs are hybridized with the extended strand in an adjacent manner, and the two SOs each comprises one label among a reporter molecule and a quencher molecule of an interactive dual label.

11. The method according to claim 1, wherein the signal is a peak provided from a melting analysis or a hybridization analysis using the extended strand and the intensity of the signal is a height or area of the peak.

12. The method according to claim 1, wherein the PTO-SNV and/or CTO is blocked at its 3'-end to prohibit its extension.

13. The method according to claim 1, wherein the upstream oligonucleotide is an upstream primer or an upstream probe.

14. The method according to claim 1, wherein the method further comprises repeating all or some of the steps (a)-(e) with denaturation between repeating cycles.

15. The method according to claim 1, wherein the method is performed to detect at least two types of SNPs; wherein the upstream oligonucleotide comprises at least two types of oligonucleotides and the PTO-SNV comprises at least two types of the PTO-SNVs.

16. The method according to claim 1, wherein the method is performed to detect a single SNP nucleotide of a plurality of SNP nucleotides found in the SNP.

17. The method according to claim 1, wherein the method is performed in the presence of a downstream primer.

18. A method for determining a SNP (single nucleotide polymorphism) genotype, comprising:
(a) hybridizing a target nucleic acid sequence containing a SNP with a primer pair comprising an upstream primer and an downstream primer and a PTO-SNV (Probing and Tagging Oligonucleotide for Single Nucleotide Variation); wherein the upstream primer and the downstream primer comprise a hybridizing nucleotide sequence complementary to the target nucleic acid sequence; the PTO-SNV comprises (i) a 3'-targeting portion comprising a hybridizing nucleotide sequence complementary to the target nucleic acid sequence, (ii) a 5'-tagging portion comprising a nucleotide sequence non-complementary to the target nucleic acid sequence, and (iii) a single nucleotide variation discrimination site comprising a nucleotide complementary to a SNP nucleotide at a SNP site of the SNP allele of interest on the target nucleic acid sequence, positioned on a 5'-end part of the 3'-targeting portion; wherein the 3'-targeting portion is hybridized with the target nucleic acid sequence and the 5'-tagging portion is not hybridized with the target nucleic acid sequence; the PTO-SNV is located between the upstream primer and the downstream primer; wherein the PTO-SNV is blocked at its 3'-end to prohibit its extension;
(b) contacting the resultant of the step (a) to a template-dependent nucleic acid polymerase having a 5' nuclease activity under conditions for extension of the primers and for cleavage of the PTO-SNV; wherein when the PTO-SNV is hybridized with the SNP allele of interest having the SNP nucleotide complementary to the single nucleotide variation discrimination site, the 5'-end part of the 3'-targeting portion forms a double strand with the target nucleic acid sequence to induce cleavage from a first initial cleavage site, and a first fragment is released; wherein when the PTO-SNV is hybridized with a different SNP allele from the SNP allele of interest having a SNP nucleotide non-complementary to the single nucleotide variation discrimination site, the 5'-end part of the 3'-targeting portion does not form a double strand with the target nucleic acid sequence to induce cleavage from a second initial cleavage site located downstream of the first initial cleavage site, and a second fragment is released; wherein the second fragment comprises an additional 3'-end portion allowing the second fragment different from the first fragment;

(c) hybridizing the fragment released from the PTO-SNV with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO-SNV and (ii) a templating portion comprising a nucleotide sequence non-complementary to the 5'-tagging portion and the 3'-targeting portion of the PTO-SNV; wherein the first fragment or the second fragment released from the PTO-SNV is hybridized with the capturing portion of the CTO;

(d) performing an extension reaction using the resultant of the step (c) and a template-dependent nucleic acid polymerase; wherein when the first fragment is hybridized with the capturing portion of the CTO, it is extended to form an extended strand comprising an extended sequence complementary to the templating portion of the CTO; wherein when the second fragment is hybridized with the capturing portion of the CTO, it is not extended;

(e) detecting a signal indicating the presence of the extended strand; wherein the signal shows higher intensity for the target nucleic acid sequence homozygous for the SNP allele of interest than that of the target nucleic acid sequence heterozygous for the SNP allele of interest, and the signal is not provided from the target nucleic acid sequence having no SNP allele of interest; and (f) determining a SNP genotype in the target nucleic acid sequence by the intensity of the signal detected in the step (e).

19. The method according to claim 18, wherein the method further comprises repeating all or some of the steps (a)-(e) with denaturation between repeating cycles.

20. A method for determining a SNP (single nucleotide polymorphism) genotype, comprising:
(a) hybridizing a target nucleic acid sequence containing a SNP with a PTO-SNV (Probing and Tagging Oligonucleotide for Single Nucleotide Variation); wherein the PTO-SNV comprises (i) a 3'-targeting portion comprising a hybridizing nucleotide sequence complementary to the target nucleic acid sequence, (ii) a 5'-tagging portion comprising a nucleotide sequence non-complementary to the target nucleic acid sequence, and (iii) a single nucleotide variation discrimination site comprising a nucleotide complementary to a SNP nucleotide at a SNP site of the SNP allele of interest on the target nucleic acid sequence, positioned on a 5'-end part of the 3'-targeting portion; wherein the 3'-targeting portion is hybridized with the target nucleic acid sequence and the 5'-tagging portion is not hybridized with the target nucleic acid sequence;

(b) contacting the resultant of the step (a) to an enzyme having a 5' nuclease activity under conditions for cleavage of the PTO-SNV; wherein when the PTO-SNV is hybridized with the SNP allele of interest having the SNP nucleotide complementary to the single nucleotide variation discrimination site, the 5'-end part of the 3'-targeting portion forms a double strand with the target nucleic acid sequence to induce cleavage from a first initial cleavage site, and a first fragment is released; wherein when the PTO-SNV is hybridized with a different SNP allele from the SNP allele of interest having a SNP nucleotide non-complementary to the single nucleotide variation discrimination site, the 5'-end part of the 3'-targeting portion does not form a double strand with the target nucleic acid sequence to induce cleavage from a second initial cleavage site located downstream of the first initial cleavage site, and a second fragment is released; wherein the second fragment comprises an additional 3'-end portion allowing the second fragment different from the first fragment;

(c) hybridizing the fragment released from the PTO-SNV with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO-SNV and (ii) a templating portion comprising a nucleotide sequence non-complementary to the 5'-tagging portion and the 3'-targeting portion of the PTO-SNV; wherein the first fragment or the second fragment released from the PTO-SNV is hybridized with the capturing portion of the CTO;

(d) performing an extension reaction using the resultant of the step (c) and a template-dependent nucleic acid polymerase; wherein when the first fragment is hybridized with the capturing portion of the CTO, it is extended to form an extended strand comprising an extended sequence complementary to the templating portion of the CTO; wherein when the second fragment is hybridized with the capturing portion of the CTO, it is not extended;

(e) detecting a signal indicating the presence of the extended strand; wherein the signal shows higher intensity for the target nucleic acid sequence homozygous for the SNP allele of interest than that of the target nucleic acid sequence heterozygous for the SNP allele of interest, and the signal is not provided from the target nucleic acid sequence having no SNP allele of interest; and (f) determining a SNP genotype in the target nucleic acid sequence by the intensity of the signal detected in the step (e).

* * * * *

SEQUENCE LISTING

```
<160> NUMBER OF SEQ ID NOS: 4

<210> SEQ ID NO 1
<211> LENGTH: 34
<212> TYPE: DNA
<213> ORGANISM: Artificial Sequence
<220> FEATURE:
<223> OTHER INFORMATION: Artificially synthesized
<220> FEATURE:
<221> NAME/KEY: misc_feature
<222> LOCATION: (19)..(24)
<223> OTHER INFORMATION: n denotes deoxyinosine

<400> SEQUENCE: 1
gcagggagct ttgaggctgn nnnnaagcac ttga                              34

<210> SEQ ID NO 2
<211> LENGTH: 35
<212> TYPE: DNA
<213> ORGANISM: Artificial Sequence
<220> FEATURE:
<223> OTHER INFORMATION: Artificially synthesized
<220> FEATURE:
<221> NAME/KEY: misc_feature
<222> LOCATION: (22)..(26)
<223> OTHER INFORMATION: n denotes deoxyinosine

<400> SEQUENCE: 2
```

```
cctcacctgg atgggaaaga tnnnnnggac gatgg                                    35

<210> SEQ ID NO 3
<211> LENGTH: 40
<212> TYPE: DNA
<213> ORGANISM: Artificial Sequence
<220> FEATURE:
<223> OTHER INFORMATION: Artificially synthesized

<400> SEQUENCE: 3
ctcctgctcg cgtactcccg cagacacctt ctccttcaag                               40

<210> SEQ ID NO 4
<211> LENGTH: 39
<212> TYPE: DNA
<213> ORGANISM: Artificial Sequence
<220> FEATURE:
<223> OTHER INFORMATION: Artificially synthesized

<400> SEQUENCE: 4
tttttttttt tttttttttt tcttatacgc gagcaggag                                39
```